(12) United States Patent
Winter et al.

(10) Patent No.: US 7,306,907 B2
(45) Date of Patent: *Dec. 11, 2007

(54) SINGLE DOMAIN LIGANDS, RECEPTORS COMPRISING SAID LIGANDS, METHODS FOR THEIR PRODUCTION, AND USE OF SAID LIGANDS AND RECEPTORS

(75) Inventors: Gregory Paul Winter, Cambridge (GB); Elizabeth Sally Ward, Cambridge (GB); Detlef Güssow, Cambridge (GB)

(73) Assignee: Cambridge Antibody Technology Limited, Cambridge (GB)

( * ) Notice: Subject to any disclaimer, the term of this patent is extended or adjusted under 35 U.S.C. 154(b) by 727 days.

This patent is subject to a terminal disclaimer.

(21) Appl. No.: 10/290,252

(22) Filed: Nov. 8, 2002

(65) Prior Publication Data

US 2003/0114659 A1   Jun. 19, 2003

Related U.S. Application Data

(60) Continuation of application No. 09/722,364, filed on Nov. 28, 2000, now Pat. No. 6,545,142, which is a continuation of application No. 08/470,031, filed on Jun. 6, 1995, now Pat. No. 6,248,516, which is a division of application No. 08/332,046, filed on Nov. 1, 1994, now abandoned, which is a continuation of application No. 07/796,805, filed on Nov. 25, 1991, now abandoned, which is a division of application No. 07/580,374, filed on Sep. 11, 1990, now abandoned.

(30) Foreign Application Priority Data

| Nov. 11, 1988 | (GB) | 8826444.5 |
| Mar. 16, 1989 | (GB) | 8906034.7 |
| Apr. 22, 1989 | (GB) | 8909217.5 |
| May 15, 1989 | (GB) | 8911047.2 |
| Jun. 2, 1989 | (GB) | 8912652.8 |
| Jun. 16, 1989 | (GB) | 8913900.0 |
| Aug. 15, 1989 | (GB) | 8918543.3 |
| Nov. 13, 1989 | (WO) | PCT/GB89/01344 |

(51) Int. Cl.
    *C12Q 1/68* (2006.01)
(52) U.S. Cl. .................. 435/6; 435/7.1; 435/69.6; 435/320.1; 435/489
(58) Field of Classification Search .................. 435/6, 435/69.6
See application file for complete search history.

(56) References Cited

U.S. PATENT DOCUMENTS

| 4,356,270 | A | 10/1982 | Itakura |
| 4,642,334 | A | 2/1987 | Moore et al. |
| 4,656,134 | A | 4/1987 | Ringold |
| 4,683,195 | A | 7/1987 | Mullis et al. |
| 4,683,202 | A | 7/1987 | Mullis |
| 4,704,692 | A | 11/1987 | Ladner |
| 4,711,845 | A | 12/1987 | Gelfand et al. |
| 4,714,681 | A | 12/1987 | Reading |
| 4,800,159 | A | 1/1989 | Mullis et al. |
| 4,806,471 | A | 2/1989 | Molin et al. |
| 4,816,397 | A | 3/1989 | Boss et al. |
| 4,889,818 | A | 12/1989 | Gelfand et al. |
| 4,937,193 | A | 6/1990 | Hinchliffe et al. |
| 4,946,786 | A | 8/1990 | Tabor et al. |
| 4,959,317 | A | 9/1990 | Sauer |
| 4,965,188 | A | 10/1990 | Mullis et al. |
| 4,978,743 | A | 12/1990 | Selbeck et al. |
| 4,983,728 | A | 1/1991 | Herzog et al. |
| 5,023,171 | A | 6/1991 | Ho et al. |
| 5,030,565 | A | 7/1991 | Niman et al. |
| 5,126,258 | A | 6/1992 | Lerner et al. |
| 5,229,072 | A | 7/1993 | Tarancon |
| 5,229,292 | A | 7/1993 | Stock et al. |
| 6,248,516 | B1 | 6/2001 | Winter et al. |

FOREIGN PATENT DOCUMENTS

| CA | 2016841 | 11/1990 |
| CA | 2019323 | 12/1990 |
| EP | A 0 120 694 | 10/1984 |
| EP | A 0 125 023 | 11/1984 |
| EP | 0 171 496 | 2/1986 |
| EP | 0 173 494 | 3/1986 |
| EP | 0 194 276 B1 | 9/1986 |
| EP | 0 201 184 B1 | 12/1986 |
| EP | A 0 200 362 | 12/1986 |

(Continued)

OTHER PUBLICATIONS

Inbar et al., PNAS-USA, 69, 2659-2662, 1972.

(Continued)

*Primary Examiner*—James Ketter
(74) *Attorney, Agent, or Firm*—Nixon & Vanderhye P.C.

(57) ABSTRACT

The present invention relates to single domain ligands derived from molecules in the immunoglobulin (Ig) superfamily, receptors comprising at least one such ligand, methods for cloning, amplifying and expressing DNA sequences encoding such ligands, preferably using the polymerase chain reaction, methods for the use of said DNA sequences in the production of Ig-type molecules and said ligands or receptors, and the use of said ligands or receptors in therapy, diagnosis or catalysis.

9 Claims, 23 Drawing Sheets

FOREIGN PATENT DOCUMENTS

| | | |
|---|---|---|
| EP | A 0 239 400 | 9/1987 |
| EP | 0 368 684 | 5/1990 |
| GB | 2 137 631 | 10/1984 |
| JP | 61-104788 | 5/1986 |
| JP | 63-152984 | 6/1988 |
| WO | WO 86/01533 | 3/1986 |
| WO | WO 87/02671 | 5/1987 |
| WO | WO-A 88/01649 | 3/1988 |
| WO | WO 88/06630 | 9/1988 |
| WO | WO 88/09344 | 12/1988 |
| WO | WO 89/00999 | 2/1989 |
| WO | WO 90/14424 | 11/1990 |
| WO | WO 90/14430 | 11/1990 |
| WO | WO 90/14443 | 11/1990 |
| WO | WO-A 97/08320 | 3/1997 |

OTHER PUBLICATIONS

Amit et al., Science, 233, 747-753, 1986.
Satow et al., J. Mol. Biol. 190, 593-604, 1986.
Colman et al., Nature, 326, 358-363, 1987.
Sheriff et al., PNAS-USA, 84, 8075-8079, 1987.
Padin et al., PNAS-USA, 86, 5938-5942, 1989.
Skerra and Plückthun, Science, 240, 1038-1041, 1988.
Bird et al., Science, 242, 423-426, 1988.
Huston et al., PNAS-USA, 85, 5879-5833, 1988.
Porter et al., J. Cell. Physiology, 67, 51-64, 1966.
Jaton et al., Biochemistry, 7, 4185-4195, 1968.
Rockey, J., J. Exp. Med., 125, 249-275, 1967.
Stevenson, Biochem. J., 133, 827-836, 1973.
Edmundson et al., Biochemistry, 14, 3953-3961, 1975.
Rossmann et al., Nature, 317, 145-153, 1985.
Saiki et al., Science, 230, 1350-1354, 1985.
Larrick, et al., Biochem, Biophys. Res. Comm., 160, 1250-1265, 1989.
Orlandi et al., PNAS-USA, 86, 3833-1989.
Yon and Fried, Nuc. Acids, Res., 17, 4895, 1989.
Fields and Song, Nature, 340, 245-246, 1989.
Baldwin and Schultz, Science, 245, 1104-1107, 1989.
Menard et al., Cancer Res., 43, 1295-1300, 1983.
Bosslet et al., Eur. J. Nuc. Med., 14, 523-528, 1988.
Bosslet et al., Cancer Immunol. Immunother., 23, 185-191, 1986.
Bremer et al., J. Biol. Chem., 259, 14773-14777, 1984.
Griffiths & Milstein, Hybridoma Technology in the Biosciences and Medicine, 103-115, 1985.
Jones et al., Nature, 321, 522-525, 1986.
Zoller & Smith, Nuc. Acids Res., 10, 6487-6500, 1982.
Carter et al., Nuc. Acids Res., 13, 4431-4443, 1985.
Sanger et al., PNAS-USA, 74, 5463-5467, 1977.
Yannisch-Perron et al., Gene, 33, 103-119, 1985.
Riechmann et al., Nature, 332, 323-327, 1988.
Kearney et al., J. Immunol., 123, 1548-1550, 1979.
Potter et al., PNAS-USA, 81, 7161-7165, 1984.
Galfre & Milstein, Meth. Enzyme., 73, 1-47, 1981.
Laemmli, Nature, 227, 680-685, 1970.
Better et al., Science, 240, 1041-1043, 1988.
Lei et al., J. Bacteriol., 169, 4379-4383, 1987.
Verhoeyen et al., Science, 239, 1534-1536, 1988.
Gronenborn, Mol. Gen. Genet, 148, 243-250, 1976.
Dagert et al., Gene, 6, 23-28, 1974.
Hanahan, J. Mol. Biol., 166, 551-580, 1983.
Chaidaroglou et al., Biochem., 27, 8338-8343, 1988.
Grodberg and Dunn, J., Journal of Bacteriol., 170, 1245-1253, 1988.
Miller, R.a. et al., Blood, 62, 988-995, 1983.
Carson et al., Advances in Immunology, 38, 275-311, 1986.
Morrison, S.L. et al., Proc. Natl. Acad. Sci. USA, 81, 6851-6855, 1984.
Boulianne, G.L. et al., Nature, 312, 643-646, 1984.
Neuberger, M. et al., Nature, 314, 268-270, 1985.
Oi et al., Proc. Natl. Acad. Sci. USA, 80, 825-829, 1983.
Ochi, A. et al., Nature, 302, 340-342, 1983.
Neuberger, M.S., EMBO J. 2, 1373-1378, 1983.
Scharf, S.J. et al., Science, 233, 1076-1078, 1986.
Lee, C.C. et al., Science, 239, 1288-1291, 1988.
Bruggemann, M. et al., J. Exp. Med., 166, 1351-1361, 1987.
Staden, R., Nucleic Acids Res., 14, 217-231, 1986.
Saiki, R. K. et al., Science, 239, 487-491, 1988.
Kramer, B. et al., Cell, 38, 879-887, 1984.
Bosslet et al., Cancer, 36, 75-84, 1985.
Mariuzza et al., J. Mol. Biol., 170, 1055-1058, 1983.
Chiang et al., Biotechniques, 7, 260-266, 1989.
Winter et al., Nucl. Acids, Res., 9, 237-245, 1981.
Brodeur et al., Eur. J. Immunol. I—14, 922-930, 1984.
Brown et al., Methods Enzymol., 68, 109-151, 1979.
Chomczynski et al., Analytical Biochem, 162, 156-159, 1987.
Cohen et al., Proc. Natl. Acad. Sci. USA, 69 (8): 2110-2114, 1972.
Dildrop, Immunology Today, 5(4): 85-86, 1984.
DiLella et al., Methods in Enzymol., 152, 199-212, 1987.
Frischauf, A., Methods in Enzymol., 152, 183-189, 1987.
Frischauf, A., Methods in Enzymol., 152, 190-199, 1987.
Gearhart et al., Nature, 291, 29-34, 1981.
Ginsberg et al., The Journal of Bio. Chem., 262(12): 5437-5440, 1987.
Graham et al., Virology, 52, 456-467, 1973.
Green et al., Cell, 28, 477-487, 1982.
Hermann et al., Methods in Enzymol., 152, 180-183, 1987.
Holmes et al., Analytical Biochem., 114, 193-197, 1981.
Janda et al., Science, 241, 1188-1191, 1988.
Janda et al., Science, 244, 437-440, 1989.
Joyce et al., Nucleic Acids Research, 17(2): 711-722, 1989.
Krieg et al., Nucleic Acids Research, 12(18): 7057-7070, 1984.
Lai et al., Nature, 331, 543-546, 1988.
Martin et al., Nuc. Acids Research, 13(24): 8927-8938, 1985.
Movva et al., J. Biol. Chem., 255(1): 27-29, 1980.
Narang et al., Meth. Enzymol., 68, 90-98, 1979.
Niman et al., Proc. Natl. Acad. Sci. USA, 80, 4949-4953, 1983.
Ohtsuka et al., J. Biol. Chem., 260(5): 2605-2608, 1985.
Pollack et al., Science, 234, 1570-1572, 1986.
Ruoslahti et al., Science, 238, 491-497, 1987.
Shine et al., Nature, 254, 34-38, 1975.
Short et al., Nucleic Acids Research, 16(15): 7583-7600, 1988.
Sorge et al., Mol. Cell. Biol., 4(9): 1730-1737, 1984.
Southern et al., J. Mol. Appl. Genet., 1, 327-341, 1982.
Southern, E., J. Mol. Biol. 98, 503-517, 1975.
Studier et al., J. Mol. Biol., 189, 113-130, 1986.
Suzuki et al., Proc. Natl. Acad. Sci. USA, 83, 8614-8618, 1986.
Takahashi et al., Proc. Natl. Acad. Sci. USA, 82, 1931-1935, 1985.
Tramontano et al., Science, 234, 1566-1569, 1986.
Wigler et al., Proc. Natl. Acad. Sci. USA, 76(3): 1373-1376, 1979.
Sastry et al., PNAS USA, 86, 5728-5732, 1989.
Kokubu et al., The EMBO Journal, vol. 7, No. 7, 1979-1988, (1988).
Schwager et al., PNAS USA, vol. 85, pp. 2245-2249 (Apr. 1988).
Roth et al., Science (Sep. 9, 1988) 241: 1354-1358.
McCormack et al., The Journal of Immunology, vol. 141, 2063-2071, No. 6, Sep. 15, 1988.
Gubler et al., Gene, 25, (1983) 263-269.
Land et al., Nucleic Acids Research, vol. 9, No. 10 (1981).
Larrick et al., Progress in Biotechnology, vol. 5, In Vitro Immunization in Hybridoma Tech., (1988) 231-246.
Glockshuber et al., Biochemistry (1992) 31: 1270-1279.
Proba et al., J. Mol. Biol., (1997) 265: 161-172.
Proba et al., J. Mol. Biol., (1998) 275: 245-253.
Kabat et al., Sequences of Proteins of Immunological Interest, U.S. Dept. HHS, 1987, pp. 494-525.
Hunkapiller et al., Nature, 323, 1986.
Amzel et al., Ann. Rev. Biochem. 48: 961-97, 1979.
Cioe et al., Proc. Natl. Acad. Sci., 82: 1367-1371, 1985.
Tonegawa, Nature 302: 575-581, 1983.
Honjo, Ann. Rev. Immunol., 1: 499-503, 1983.
Mack et al., Proc. Natl. Acad. Sci, 85: 6977-6981, 1988.
Kaczmarek et al., Journal of Cellular Physiology, 132: 545-551, 1987.
Cioe et al., Blood, 70(4): 915-920, 1987.
Curtis et al., Gene, 25: 325-332, 1983.

Akowitz et al., Gene, 81: 295-306, 1989.
Ausubel et al., Current Protocols in Molecular Biology, 1987.
Aviv et al., Proc. Natl. Acad. Sci., 69: 1408-1412, 1972.
Barbas et al., Proc. Natl. Acad. Sci., 88: 7978-7983, 1991.
Belyavsky et al., Nucleic Acids Research, 17(8): 2919-2932, 1989.
Berent et al., BioTechniques, 3: 208-220, 1985.
Bolton et al., Biochem J. 133: 529-539, 1973.
Chang et al., Proc. Natl. Acad. Sci., 84: 5640-5644, 1987.
Chang et al., J. Immun., 147: 3610-3614, 1991.
Clackson et al., Nature, 352: 624-628, 1991.
Delaloye et al., J. Clin. Invest., 77: 301-311, 1986.
Field et al., Molecular and Cellular Biology, 8(5): 2159-2165, 1988.
Garrett et al., Journal of Virology, 44(3): 886-892, 1982.
Guarente et al., Science, 209: 1428-1430, 1980.
Guarente et al., Cell, 20: 543-553, 1980.
Gold et al., Ann. Rev. Microbiol., 35: 365-403, 1981.
Ho et al., Gene, 77: 51-59, 1989.
Hoogenboom et al., Nucleic Acids Research, 19(15): 4133-4137, 1991.
Huse et al., Science, 246: 1275-1281, 1988.
Huse et al., Antibody Engineering: A Practical Guide, 103-120.
Erlich et al., PCR Protocols, pp. 261-271, 1990.
Iverson et al., Cold Spring Harbor Symposia on Quantitative Biology, vol. LIV, pp. 273-281, 1989.
Jiang et al., Oncogene, 4, 923-928, 1989.
Kang et al., Proc. Natl. Acad. Sci., 88: 4363-4366, 1991.
Li et al., Proc. Natl. Acad. Sci., 85: 7685-7689, 1988.
Loh et al., Science, 243: 217-220, 1989.
Marx, Science, 246: 1250-1251, 1989.
McCafferty et al., Nature, 348: 552-554, 1990.
Moore, Clinical Chemistry, 35(9): 1849-1853, 1989.
McLeod et al., Molecular and Cellular Biology, 6(10): 3357-3367, 1986.
Morrison, Science, 229: 1202-1207, 1985.
Mullinax et al., Proc. Natl. Acad. Sci., 87: 8095-8099, 1990.
Oliver, *Escherichia coli* and *Salmonella typhimurium*, 1: 56-69, 1987.
Neuberger et al., Nature, 312: 604-608, 1984.
Ohara et al., Proc. Natl. Acad. Sci., 86: 5673-5677, 1989.
Sachs, Fundamental Immunology, pp. 303-377, 1984.
Raab et al., J. Mol. Biol., 199: 95-105, 1988.
Rathbun et al., Nature, 342: 863-864, 1989.
Roberts et al., Proc. Natl. Acad. Sci., 76(2): 760-764, 1979.
Roberts et al., Proc. Natl. Acad. Sci., 76(11): 5596-5600, 1979.
Header et al., Virology, 43: 607-622, 1971.
Senecoff et al., Proc. Natl. Acad. Sci., 82: 7270-7274, 1985.
Sommer et al., Nucleic Acids Research, 17(16): 6749, 1989.
Taniguchi et al., J. Mol. Biol., 118(4): 533-564, 1978.
Vitetta et al., Science, 219: 644-650, 1983.
Ward et al., Nature, 341: 544-546, 1989.
Wahl et al., The Journal of Nuclear Medicine, 24(4): 316-325, 1983.
Weisberg et al., Site-specific Recombination in Phage Lambda, Cold Spring Manbar Lab., pp. 211-217, 1983.
Winter et al., Nature, 349: 293-299, 1991.
Zalcberg, Am. J. Clin. Oncol., 8: 481-489, 1985.
Orlandi et al., UCLA Symposia on Molecular & Cellular Biology, p. 90, No. A325, 1989.
Berg, Mobile DNA, American Society for Microbiology, 1989 (Table of Contents only).

Early et al., Genetics Engineering Principles and Methods, 3: 157-188, 1981.
Erlich, PCR Technology, 1989 (Table of Contents only).
Haber, Ann. Rev. Med., 37: 249-61, 1986.
Gussow et al., Cold Spring Harbor Symposia, vol. LIV, 1989.
Harlow et al., Antibodies: A Laboratory Manual, 1988 (Table of Contents only).
Huse, Ciba Foundation Symposium, 159: 91-102, 1991.
Jencks, Catalysis in Chemistry and Enzymology, 1969 (Table of Contents only).
Rennie, Scientific American, pp. 62-65, 1990.
Gingeras et al., PCR Protocols: A Guide to Methods and Applications, pp. 245-252, 1990.
Thorpe et al., Monoclonal Antibodies in Clinical Medicine, pp. 167-201, 1982.
Vitetta, Intl. Symposium of the Princess Takamatsu Cancer Research Fund, pp. 333-340, 1988.
Chamberlain et al., The Enzymes, vol. XV, Part B (Table of Contents only).
Rabbitts, Declaration in the Matter of European Patent 0 368 864.
Neuberger et al., Phil. Trans. R. Soc. Lond. 317: 425-432, 1986.
Neuberger, Trends in Biochemical Sciences 10(9): 347-349, 1985.
Neuberger et al., 8th Int. Biotech Symposium, Ed. G. Durant et al. Soc. Francaise de Microbiology, pp. 792-799, Paris, 1988.
Neuberger et al., Immunology Today 9(9): 278-281, 1988.
Neuberger et al., Protein Engineering 311-317, 1986.
Winter et al., Investigation and Exploitation of Antibody Combining Sites 139-140, 1985.
Bruggemann et al., Behring Inst. Mitt., No. 87, 21-24, 1990.
I. Roitt, et al., "The Generation of Antibody Diversity," Immunology, Gower Medical Publishing pp. 9.1-9.11 (1985).
Appeal Brief of Opposition to EP-B-0368 684, filed by MorphoSys and submitted to the Technical Appeal Board of European Patent Office on Oct. 9, 2000.
M. Chua, et al., "Germ-Line Affinity and Germ-Line Variable Region Genes in the B Cell Response", The Journal of Immunology, 138(4):1281-1288 (1987).
E. Kabat, "Antibody Complementarity and Antibody Structure," Journal of Immunology, 141(7 Suppl):S25-36.
H. Kimura, et al., "Sequences of the $V_H$ and $V_L$ Regions of Murine Monoclonal Antibodies Against 3-Fucosyllactosamine," The Journal of Immunology, 140(4):1212-1217 (1988).
Dolby et al., PNAS USA 77(10): 6027-6031, 1980.
Sharon et al., Nature 309: 364-367, 1984.
Takeda et al., Nature 314: 452-454, 1985.
Maniatis et al., Molecular Cloning: A Laboratory Manual, 1982 (Table of Contents only).
Verhoeyen, Bio Essays vol. 8, No. 2—Feb./Mar. 1988.
Chothia et al, (1986) Science, 233 (4765), 755-758.
Chothia & Lesk (1987) J. Mol. Biol., 196, 901-917.
Chothia et al., (1989) Nature, 342, 877-883.
Interlocutory Decision European Patent No. 368,684; Mar. 9, 1994 EP in Opposition Proceedings (Article 102(3) and 106(3) EPC dated May 20, 2000 from Oral Proceedings held Oct. 14, 1999 in file of European Patent No. 368,684.
Hunkapiller et al, "The Growing Immunoglobulin Gene Superfamily", Nature, vol. 323, Sep. 4, 1986, pp. 15-16.

Rearranged heavy chain variable gene (DNA)
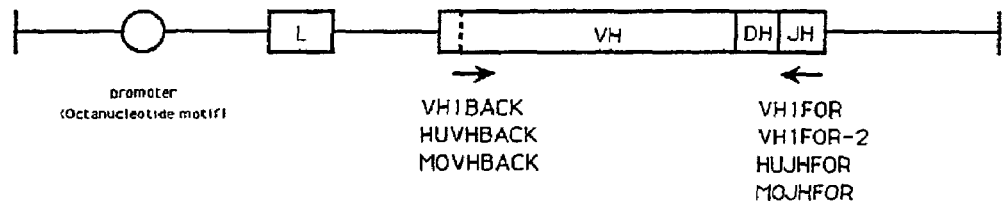
Unrearranged heavy chain variable gene (DNA)
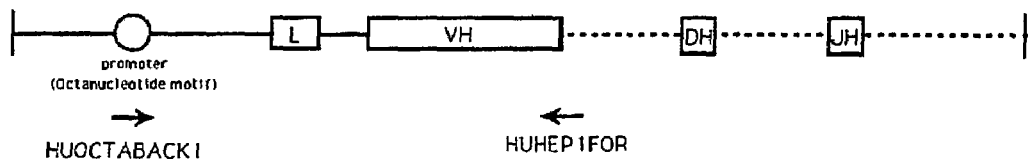
Rearranged heavy chain variable gene (mRNA)
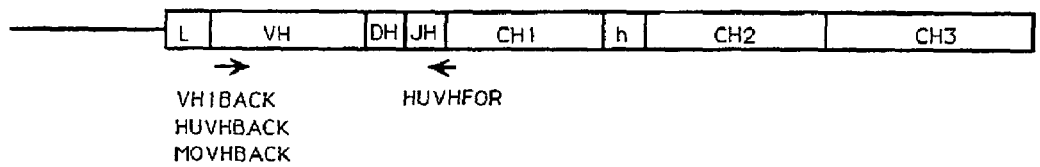
Rearranged light chain variable gene (DNA)
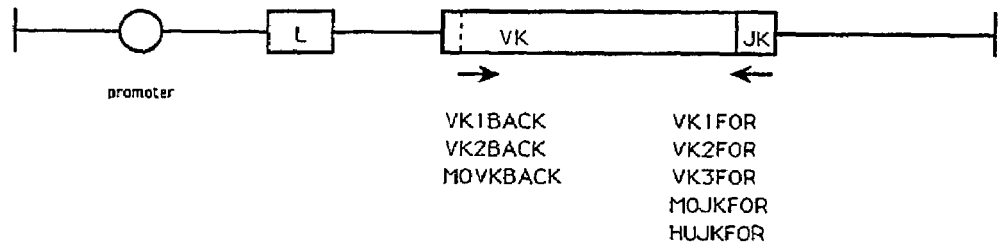
FIG. 1

M13 VHPCR1

HinD III(a)
|
AAGCTTATGAATATGCAAATCCTCTGAATCTACATGGTAAATATAGGTTTGTCTATACCA
　　　10　　　　20　　　　30　　　　40　　　　50　　　　60

CAAACAGAAAAACATGAGATCACAGTTCTCTCTACAGTTACTGAGCACACAGGACCTCAC
　　　70　　　　80　　　　90　　　100　　　110　　　120

M　G　W　S　C　I　I　L　F　L　V　A　T　A　T
CATGGGATGGAGCTGTATCATCCTCTTCTTGGTAGCAACAGCTACAGGTAAGGGGCTCAC
　　　130　　　140　　　150　　　160　　　170　　　180

AGTAGCAGGCTTGAGGTCTGGACATATATATGGGTGACAATGACATCCACTTTGCCTTTC
　　　190　　　200　　　210　　　220　　　230　　　240

PstI
　　　　　　　　　　　　　1　　　　5|　　　　10
　　　　　G　V　H　S　Q　V　Q　L　Q　E　S　G　P　G　L　V　R　P
TCTCCACAGGTGTCCACTCCCAGGTCCAACTGCAGGAGAGCGGTCCAGGTCTTGTGAGAC
　　　250　　　260　　　270　　　280　　　290　　　300

CDR1
　15　　　　　20　　　　　25　　　　　30
　S　Q　T　L　S　L　T　C　T　V　S　G　S　T　F　S　*S*　*Y*　*W*　*M*
CTAGCCAGACCCTGAGCCTGACCTGCACCGTGTCTGGCAGCACCTTCAGCAGCTACTGGA
　　　310　　　320　　　330　　　340　　　350　　　360

CDR2
　35　　　　　40　　　　　45　　　　　50
　*H*　W　V　R　Q　P　P　G　R　G　L　E　W　I　G　*R*　*I*　*D*　*P*　*N*
TGCACTGGGTGAGACAGCCACCTGGACGAGGTCTTGAGTGGATTGGAAGGATTGATCCTA
　　　370　　　380　　　390　　　400　　　410　　　420

55　　　　　60　　　　　65　　　　　70
　*S*　*G*　*G*　*T*　*K*　*Y*　*N*　*E*　*K*　*F*　*K*　S　R　V　T　M　L　V　D　T
ATAGTGGTGGTACTAAGTACAATGAGAAGTTCAAGAGCAGAGTGACAATGCTGGTAGACA
　　　430　　　440　　　450　　　460　　　470　　　480

75　　　　　80　　　　　85　　　　　90
　S　K　N　Q　F　S　L　R　L　S　S　V　T　A　A　D　T　A　V　Y
CCAGCAAGAACCAGTTCAGCCTGAGACTCAGCAGCGTGACAGCCGCCGACACCGCGGTCT
　　　490　　　500　　　510　　　520　　　530　　　540

CDR3
　95　　　　　100　　　　105　　　　　110
　Y　C　A　R　*Y*　*D*　*Y*　*Y*　*G*　*S*　*S*　*Y*　*F*　*D*　*Y*　W　G　Q　G　T
ATTATTGTGCAAGATACGATTACTACGGTAGTAGCTACTTTGACTACTGGGGCCAAGGGA
　　　550　　　560　　　570　　　580　　　590　　　600

BstEII
115　|　　　　120
　T　V　T　V　S　S
CCACGGTCACCGTCTCCTCAGGTGAGTCCTTACAACCTCTCTCTTCTATTCAGCTTAAAT
　　　610　　　620　　　630　　　640　　　650　　　660

AGATTTTACTGCATTTGTTGGGGGGGAAATGTGTGTATCTGAATTTCAGGTCATGAAGGA
　　　670　　　680　　　690　　　700　　　710　　　720

CTAGGGACACCTTGGGAGTCAGAAAGGGTCATTGGGAGCCCGGGCTGATGCAGACAGACA
　　　730　　　740　　　750　　　760　　　770　　　780

BamHI
　　　　　　　　　　　　　　　　　　　　　　|
TCCTCAGCTCCCAGACTTCATGGCCAGAGATTTATAG
　　　790　　　800　　　810

FIG. 3

M13 VkPCR1

```
HinD III
|
AAGCTTATGAATATGCAAATCCTCTGAATCTACATGGTAAATATAGGTTTGTCTATACCA
     38        48        58        68        78        88

CAAACAGAAAAACATGAGATCACAGTTCTCTCTACAGTTACTGAGCACACAGGACCTCAC
     98       108       118       128       138       148

M  G  W  S  C  I  I  L  F  L  V  A  T  A  T
CATGGGATGGAGCTGTATCATCCTCTTCTTGGTAGCAACAGCTACAGGTAAGGGGCTCAC
    158       168       178       188       198       208

AGTAGCAGGCTTGAGGTCTGGACATATATATGGGTGACAATGACATCCACTTTGCCTTTC
    218       228       238       248       258       268

Pvu II
                    1              5                 10
            G  V  H  S  D  I  Q  L  T  Q  S  P  S  S  L  S  A  S
TCTCCACAGGTGTCCACTCCGACATCCAGCTGACCCAGAGCCCAAGCAGCCTGAGCGCCA
    278       288       298       308       318       328

CDR1
     15                20               25                30
      V  G  D  R  V  T  I  T  C  R  A  S  G  N  I  H  N  Y  L  A
GCGTGGGTGACAGAGTGACCATCACCTGTAGAGCCAGCGGTAACATCCACAACTACCTGG
    338       348       358       368       378       388

CDR2
   35                40               45                50
    W  Y  Q  Q  K  P  G  K  A  P  K  L  L  I  Y  Y  T  T  T  L
CTTGGTACCAGCAGAAGCCAGGTAAGGCTCCAAAGCTGCTGATCTACTACACCACCACCC
    398       408       418       428       438       448

55                60               65                70
     A  D  G  V  P  S  R  F  S  G  S  G  S  G  T  D  F  T  F  T
TGGCTGACGGTGTGCCAAGCAGATTCAGCGGTAGCGGTAGCGGTACCGACTTCACCTTCA
    458       468       478       488       498       508

CDR3
   75                80               85                90
    I  S  S  L  Q  P  E  D  I  A  T  Y  Y  C  Q  H  F  W  S  T
CCATCAGCAGCCTCCAGCCAGAGGACATCGCCACCTACTACTGCCAGCACTTCTGGAGCA
    518       528       538       548       558       568

Bcl I (requires dam⁻ host)
                                    |
   95                100             105     108
    P  R  T  F  G  Q  G  T  K  V  V  I  K  R
CCCCAAGGACGTTCGGCCAAGGGACCAAGGTGGTGATCAAACGTGAGTAGAATTTAAACT
    578       588       598       608       618       628

BamHI
              |
TTGCTTCCTCAGTTGGATCC
    638       648
```

FIG. 5

Sequence of MBr1 VH

```
                                              Splice        -1
                                               ↓ G   V   H   S
                                                 AGGTGTCCACTCC
 1         PstI            10                            20
 Q   V   Q   L   Q   E   S   G   T   E   L   A   S   P   G   A   S   V   T   L
CAGGTCCAACTGCAGGAGTCAGGAACTGAGCTGGCGAGTCCTGGGGCATCAGTGACACTG
    VH1BACK SITE
                          30          CDR1                40
 S   C   K   A   S   G   Y   T   F   T  [D   H   I   N]  W   V   K   K   R
TCCTGCAAGGCTTCTGGCTACACATTTACTGACCATATTAATAAATTGGGTAAAAAAGAGG
                                    52a 53         CDR2
 P   G   Q   G   L   E   W   I   G  [R   I   Y   P   V   S   G   V   T   N   Y
CCTGGACAGGGCCTTGAGTGGATTGGAAGGATTTATCCAGTAAGTGGTGTAACTAACTAC
 60     CDR2         65              70
 N   Q   K   F   M   G]  K   A   T   F   S   V   D   R   S   S   N   T   V   Y
AATCAAAAATTCATGGGCAAGGCCACATTCTCTGTAGACCGGTCCTCCAACACAGTGTAC
 80          82A B   C  83                90                    CDR3
 M   V   L   N   S   L   T   S   E   D   P   A   V   Y   Y   C   G   R  [G   F
ATGGTGTTGAACAGTCTGACATCTGAGGACCCTGCTGTCTATTACTGTGGAAGGGGCTTT
      CDR3   103                 BstEII         Splice
 D   F   D   Y] W   G   Q   G   T   T   V   T   V   S   S↓
GATTTTGACTACTGGGGCCAAGGGACCACGGTCACCGTCTCCTCAGGT......
              VH1FOR SITE
```

Sequence of MBr1 VK

```
                                              Splice        -1
                                               ↓ G   V   H   S
                                                 AGGTGTCCACTCC
 1        PvuII            10                            20
 D   I   Q   L   T   Q   S   P   P   S   L   T   V   S   V   G   E   R   V   T
GACATTCAGCTGACCCAGTCTCCACCATCCCTGACTGTGTCAGTAGGAGAGAGGGTCACT
    VK1BACK SITE
              27A B   C   D   E   F         CDR1
 I   S   C  [K   S   N   Q   N   L   L   W   S   G   N   R   R   Y   C   L   G]
ATCAGTTGCAAATCCAATCAGAATCTTTTATGGAGTGGAAACCGAAGGTACTGTTTGGC
 35              40                           50          CDR2
 W   H   Q   W   K   P   G   Q   T   P   T   P   L   I   T  [W   T   S   D   R
TGGCACCAGTGGAAACCAGGGCAAACTCCTACACCGTTGATCACCTGGACATCTGATAGG
                 60                              70
 F   S]  G   V   P   D   R   F   I   G   S   G   S   V   T   D   F   T   L   T
TTCTCTGGAGTCCCTGATCGTTTCATAGGCAGTGGATCTGTGACAGATTTCACTCTGACC
                80                              90          CDR3
 I   S   S   V   Q   A   E   D   V   A   V   Y   F   C   Q  [Q   H   L   D   L
ATCAGCAGTGTGCAGGCTGAAGATGTGGCAGTTTATTTCTGTCAGCAACATTTGGACCTT
 95              100           BglII/BclI Splice
 P   Y   T]  F   G   G   G   T   K   L   E   I   K↓
CCGTACACGTTCGGAGGGGGGACCAAGCTGGAGATCAAACGTGAG
               VK1FOR SITE
```

FIG. 6

α-Lys 17
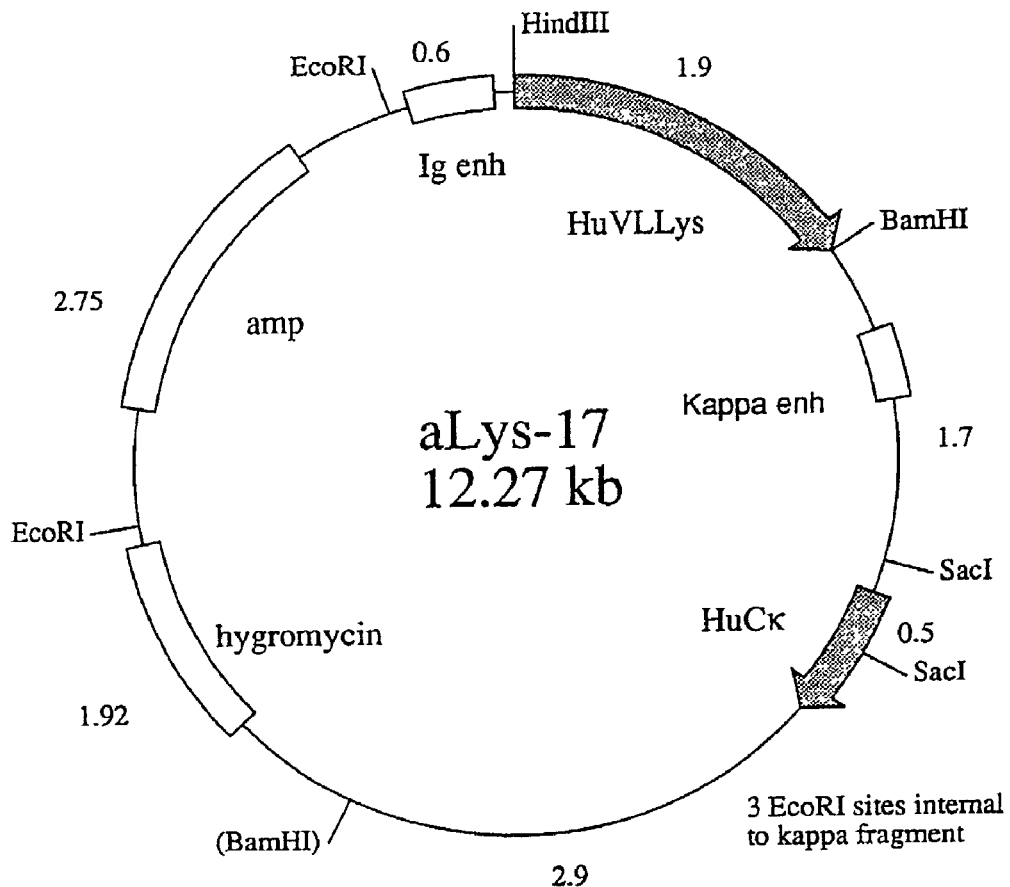
FIG. 8
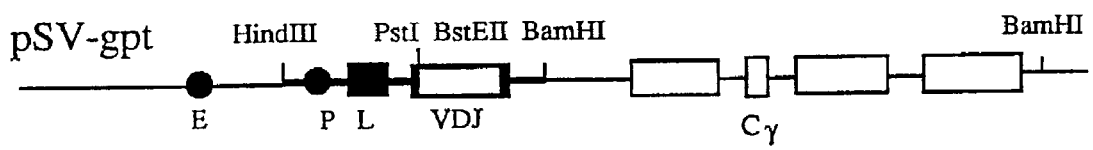
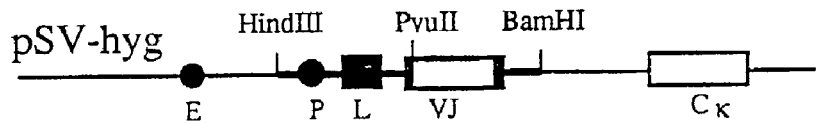
FIG. 9

|  | FR1 | CDR 1 | FR2 | CDR 2 |
|---|---|---|---|---|
| KABAT IA | | | | |
| A07 | PGLVKPSQSLSLTCSVTGYSIT | SGYYWN | WIRQFPGNKLEWMG | YISYDGSNNYNPSLKN |
| A09 | PGLVKPSQSLFLTCSITGFPIT | SGYYWI | WIRQSPGKPLEWMG | YITHSGETFYNPSLQS |
| E03 | PGLVKPSQSLSLTCSVTGYSIT | SGYYWN | WIRQFPGNKLEWMG | YISYDGSNNYNPSLKN |
| G01 | PGLVKPSQSLSLTCSVTGYSIT | SGYYWN | WIRQFPGNKLEWMG | YISYDGSNNYNPSLKN |
| KABAT IB | | | | |
| A06 | PVLVAPSQSLSITCAVSDFSLT | NYGVL | WVRQPPGKGLEWLG | VIWAGGITNYNSALMS |
| 25G07 | PGLVQPSQSLSITCTVSGFSLT | SYGVH | WVRQSPGKGLEWLG | VIWSGGSTDYNAAFIS |
| B03 | PGLVAPSQSLSITCTVSGFSLT | SYGVD | WVRQPPGKGLEWLG | VIWGGGSTNYNSALMS |
| G03 | PGLVQPSQSLSITCTVSGFSLT | SYGVH | WVRQSPGKGLEWLG | VIWSGGSTDYNAAFIS |
| H09 | PVLVAPSQSLSITCTVSGFSLT | SYGVH | WVRQPPGKGLEWLG | VIWAGGSTNYNSALMS |
| 25C10 | PGLVAPSQSLSITCTVSGFSLT | SYAIS | WVRQPPGKGLEWLG | VIWTGGGTNYNSALKS |
| A12 | PGLVAPSQSLSITCTVSGFSLT | SYAIS | WVRQPPGKGLEWLG | VIWTGGGTNYNSALKS |
| A08 | PGLVAPSQSLSITCTVSGFSLT | SYGVH | WVRQPPGKGLEW** | *****GSTTYNSALKS |
| 25G08 | PGLVQPSQSLSITCTVSGFSLT | SYDVD | WVRQSPGKGLEWLG | VIWGGGSTNYNSALKS |
| A03 | PGLVQPSQSLSITCTVSGFSLT | SYGVH | WVRQSPGKGLEWLG | VIWSGGSTDYNAAFIS |
| C07 | PVLVAPSQSLSITCTVSGFSLT | SYGVH | WVRQPPGKGLEWLG | VIWAGGSTNYNSALMS |
| H04 | PGLVAPSQSLSITCTVSGFSLT | SYGVD | WVRQSPGKGLEWLG | VIWGVGSTNYNSALKS |
| KABAT IIA | | | | |
| E04 | PELVRPGVSVKISCKGSGYTFT | DYAMH | WVKQSHAKSLEWIG | VISTYYGDASYNQKFKD |
| H07 | PELVRPGVSVKISCKGSGYTFT | DYAMH | WVKQSHAKSLEWIG | VISTYYGDASYNQKFKD |
| KABAT IIB | | | | |
| A02 | AELVMPGASVKLSCKASGYTFT | SYWMH | WVKQRPGQGLEWIG | EIDPSDSYTNYNQKFKG |
| B04 | AELVKPGASVKMSCKASGYTFT | SYWIT | WVKQRPGQGLEWIG | DIYPGSGSTNYNEKFKS |
| C05 | AELVKPGASVKLSCKASGYTFT | SYWMH | WVKQRPGRGLEWIG | RIDPNSGGTKYNEKFKS |
| C09 | AELVKPGASLKLSCKASGYTFT | SYWMH | WVKQRPGQGLEWIG | EINPSNGGTNYDEKFKS |
| D06 | ASLVKPGASVKMSCKASGYTFT | SYWIT | WVKQRPGQGLEWIG | DIYPGSGSTNYNEKFKS |
| D08 | PELVRPGASVKLSCKASGYTFT | SYWMH | WVKQRPGQGLEWIG | EINPSNGGTNYNEKFKS |
| E07 | AELVRPGASVKLSCKASGYTFT | DYEMH | WVKQTPVHGLEWIG | AIDPETGGTAYNQKFKG |
| G08 | PELVKPGASVKISCKASGYTFT | DYYIN | WVKQRPGQGLEWIG | WIYPGSGNTKYNEKFKG |
| G10 | AELVKPGASVKVSCKASGYTFT | SYWMH | WVKQRPGQGLEWIG | RIHPSDSDTNYNQKFKS |
| 25G09 | AELVKPGASVKMSCKASGYTFT | TYPIE | WVKQNHGKSLEWIG | NFHPYNDDTKYNEKFKG |
| F04 | TELVKPGASVKLSCKASGYTFT | SYWMH | WVKQRPGQGLEWIG | NINPSNGGTNYNQKFKG |
| H02 | AELVKPGASVKLSCKASGYTFT | SYWMH | WVKQRPGQGLEWIG | NIDPSDSETHYNQKFKD |
| H01 | AELVMPGASVKLSCKASGYTFT | SYWMH | WVKQRPGQGLEWIG | EIDPSDSYTNYN*KVQG |
| 25C05 | PELVRPGTSVKMKSCKASGYTFF | NYWMK | WV*QRPGQGLEWIG | QIFPASGSIYYNEMHKD |
| B01 | AELVKPGASVKMSCKASGYTFT | SYWIT | WVKQRPGQGLEWIG | DIYPGSGSTNYNEKFKS |
| B05 | AELVRPGSSVKLSCKDSYFAFM | RHAMH | WVKQRPGHGLEWIG | SFTMYSDATEYSENFKG |
| B11 | AELVKPGASVKMSCKASGYTFT | SYWIT | WVKQRPGQGLEWIG | DIYPGSGSTNYNEKFKS |
| KABAT III A | | | | |
| 25G05 | GGLVQAWGSLSLSCAASGFTFT | DYYMS | WVRQPPGKALEWLG | FIRNKANGYTTEYSASVKG |
| C10 | GGLVQPGGSLSLSCAASGFTFT | DYYMN | WVRQPPGKALEWLA | LIRHKANGYTMEYSASVKG |
| B07 | GGLVQPGGSLSLSCAASGFTFT | DYYMS | WVRQPPGKALEWLA | LIRNKANGYTTEYSASVKG |
| KABAT III B | | | | |
| G05 | GGLVKPGGSLKLSCAASGFTFS | DYGMH | WVRQAPEKGLEWVA | YISSGSSTIYYADTVKG |
| B12 | GGLVQPGESLKLSCESNEYEFP | SHDMS | WVR*********VA | AINSDGGSTYYPDTMER |
| D04 | GGLVQPGGSLRLSCAASGFTFS | SYAMS | WVA*APGKGLEWVS | AISGSGGSTYYADSVKG |
| D05 | GGLVQPGGSLRLSCAASGFTFS | SYAMS | WVA*APGKGLEWVS | AISGSGGSTYYADSVKG |
| F12 | GGLVQPGESWKLSCVIQQ**** | ***** | WVRQ*PEKRLELVA | AINSDGGSTYYPDTMER |
| F06 | GGLVQPGGSLRLSCAASGFTFS | SYAMS | WVA*APGKGLEWVS | AISGSGGSTYYADSAKG |
| D02 | GGLVQPGESLKLSCESNEYVIP | *HDMS | WVRQDSGE*LELVA | AINSDGGSTYYPDTMER |
| F09 | GDLVKPGGSLKLSCAASGFTFS | SYGMS | WVRQTPDKRLEWVA | TISSGGSYTYYPDSVKG |
| KABAT III C | | | | |
| E06 | GGLVQPGGSMKLSCAASGFTFS | DAWMD | WVRQSPEKGLEWVA | EIRNKANNHATYYAESVKG |
| KABAT V A | | | | |
| C04 | AELVKPGASVKLSCKASGYTFT | EYTIH | WVKQRSGQGLEWIG | WFYPGSGSIKYNEKFKD |

FIG. 10a

| FR 3 | CDR 3 | |
|---|---|---|
| RISITRDTSKNQFFLKLNSVTTEDTATYYCAR | EGNWDGFAY | |
| PISITRETSKNQFFLQLNSVTTEDTAMYYCAG | DRDKLGPWFAY | |
| RISITRDTSKNQFFLQLNSVTTEDTATYYCAR | DSSGSMDY | |
| RISITRDTSKNQFFLKLNSVTTEDTATYYCAR | VSSGYESMDY | |
| | | |
| RLSISKDTSKSQVFLKMNSLQTDDTAVYYCAK | HGDSSGYFDY | |
| RLSISKDNSKSQVFFKMNSLQADDTAIYYCAR | NDGYY | |
| RLSISKDNSKSQVFLKMNSLQTDDTAMYYCAK | LGRGYAMDY | |
| RLSISKDNSKSQVFFKMNSLQADDTAIYYCAR | KRDYDYDRGYYYAMDY | |
| RLSISKDNSKSQVFLKMNSLQTDDTAMYYCAI | YYDGSFFAY | |
| RLSISKDNSKSQVFLKMNSLQTDDTARYYCAR | EGYYYFAY | |
| RLSISKDNSKSQVFLKMNSLQTDDTARYYCAR | IYYDGSSDYYAMDY | |
| *RLSISKDNSKSQVFLKMNSLQTDDTAMYYCAR* | 13 nt. | Ps.gene/Unproducti٭ |
| RLSISKDNSKSQVFLKMNSLQTDDTAMYYCAR | 21 nt. | Unproductive |
| RLSISKDNSKSQVFFKMNSLQADDTAIYYCAR | 28 nt. | Unproductive |
| RLSISKDNSKSQVFLKMNSLQTDDTAMYYCAK | 37 nt. | Unproductive |
| RLSISKDNSKSQVFLKMNSLQTDDTAMYYCAS | 32 nt. | Unproductive |
| | | |
| KATMTVDKSSSTAYMELARLTSEDSAVYYCAR | 40 nt. | Unproductive |
| KATMTVDKSSSTAYMELARLTSEDSAVYYCAR | 22 nt. | Unproductive |
| | | |
| KATLTVDKSSSTAYMQLSSLTSEDSAVYYCVR | RGLTYAMDY | |
| KATLTVDTSSSTAYMQLSSLTSEDSAVYYCAR | YYSNYFDY | |
| KATLTVDKPSSTAYMQLSSLTSEDSAVYYCAR | PNWDHYYYGMDV | |
| KATLTVDKSSSTAYMQLSSLTSEDSAVYYCTL | LYYYAMDY | |
| KATLTVDTSSSTAYMQLSSLTSEDSAVYYCAR | SSGYDY | |
| KATLTVDKSSSTAYMQLSSLTSEDSAVYYCTI | GAARATNAY | |
| KATLTVDKSSSTAYMQLSSLTSEDSAVYYCAR | GGFAY | |
| KATLTVDTSSSTAYMQLSSLTSEDSAVYYCAR | SPMDY | |
| KATLTVDKSSSTAYMQLSSLTSEDSAVYYCAI | EVPGGFYATDY | |
| KATLTVEKSSSTVYLELSRLTSDDSAVYYCAR | MDYYGSSLWFAY | |
| KATLTVDKSSSTAYMQLSSLTSEDSAVYYCAK | TTVVAFDY | |
| KATLTVDKSSSTAYMQLSSLTSEDSAVYYCAR | KRDYSTYFDH | |
| *KATLTVDKSSSTAYMQLSSLTSEDSAVYYCAP* | TGTEFAY | Ps.gene |
| *KAAWAVDTSSSTAYMQLSSLTSEDTAVYFCL\** | 24 nt. | Ps.gene/Unproducti٭ |
| KATLTVDKPSDTAYMQLSSLTSEDSASYYCAR | 9 nt. | Unproductive |
| KATLTANTSSSTAYMELSSLTSEDSAVYYCAR | 23 nt. | Unproductive |
| KATLTVDTSSSTSYMQLSSLTSEDSAVYYCAR | 15 nt. | Unproductive |
| | | |
| RFTISRDNSQSILYLQMNALRAEDSATYYCAR | YMILGAMDY | |
| RFTISRDNSQSILYLQMNALRAEDSATYYCAR | GYYYDGSYYAMDY | |
| RFTISRDNSQSILYLQMNALRAEDSATYYCAR | 23 nt. | Unproductive |
| | | |
| RFTISRDNAKNTLFLQMTSLRSEDTAMYYCAR | AKFHLYFDY | |
| *RFIISRDNTKKTLYLQMSSLRSEDTALYYCAR* | REGVVESRLDGDV | Ps.gene |
| *RFTISRDNSKNTLYLQMNSLRAEDTAVYYCAD* | RGLHWFDP | Ps.gene |
| *RFTISRDNSKNTLYLQMNSLRAEDTAVYYCAK* | RNYGSSPFDY | Ps.gene |
| *RFTISRDNSKKTLYLQMSSLRSEDTALYYCAR* | PPMMPSY | Ps.gene |
| RFTISRDNSKNTLYLQMNSLRAEDTAVYYCAK | 43 nt. | Ps.gene/Unproducti٭ |
| *RFIISRDNTKKTLYLQMSSLRSEDTALYYCAR* | 28 nt. | Ps.gene/Unproducti٭ |
| RFTISRDNAKNTLYLQMSSLKSEDTAMYYCAR | 35 nt. | Unproductive |
| | | |
| RFTISRDDSKSRVYLQMNSLRAEDTGIYYCTG | 30 nt. | Unproductive |
| | | |
| KATLTADKSSSTVYMELSRLTSEDSAVYFCAR | HEDRDSSGYAMDY | |

FIG. 10 b

```
              CDR 2                      FRAMEWORK 3                    CDR 3

KABAT HUMAN VH1

STSTAYMELRSLRSEDTAVVYCAR       GEGWDHFDY
               HAQKFQG   RVTIRRHKSTSTAYMELSSLRSEDTAVYYCAR      GSRYGYDCSGYYYL
               GYAQKFQG  RVTMTRNTSISTATMELSSLRSEDTAVYYCAR      LAHFSGSPVDWFDP

KABAT HUMAN VH2

KHQLQPSLKS  RVTISVDTSKNQFSLKLSSVTAADTAVYYCAR     GGVVPAAIMDV
                      KS  RVTISVDTSKNQFSLKLSSVTAADTAVYYCAR     MARYYDFWSGYSAYYDY
                    SLKS  RLSISQDTSRNQFSLRLSSVTAADTAVYYCAR     HRNWGSPVHFDY
                                ESTSTAYMELSSLRSEDTAVYYCAR      DSYGDYGGHY

KABAT HUMAN VH3

ISYITSSSSYTNYADSVKG   RFTISRDNAKNSLYLQMNSLRADDTAVYYCAR   DGRFGTYSPSDY
                      SVKG   RFTISRDDSKSIAYLQVNSLKTEDTAVYYCTR   TIYYDSSGYPYW
                    YADSVKG  RFTISRDNAKNSLFLQMSSLRAEDTAFYYCAR   GIALDAFDI
                   YYADSVRD  RFTISRDNSKNTLYLQMNSLRAEDTAVYYCAK   53 NT. UNPROD REARR
                      DSVKG  RFTISRDNAKNSLYLQMNSLRDEDTAVYYCAR   DHSGTGGGGSGSYF
       VSAISGSGGSTYYADSVKG   RFTISRDNPKNTLYLQMNSLRSEDTAVYYCAR   KDNLWFDP
        AVISYDGSNKYYADSVKG   RFTISRDNSKNTLYLQMNSLRAEDTAVYYCAR   DLGGRGVVVVPAPGGRSIYYYGMDV
       GAVISYDGSNKYYADSVKG   RFTISRDNSKNTLYLQMNSLRAEDTAVYYCAS   LEGIGTIYYYGMDV
                             AKNSLYLQMNSLRAEDTAVYYCVR          DDSSSWPKHFQH
                  QYAASVKG   RFTISRDDSKNSLYLQMNSLNTEDTAVYYCVR   SGVVPYLDY

KNOWN FAMILY

AVYYCAR           DPRIAARPDYYYYMDV
                                             TAMYYCAR          GAEVVEPTARYYYGLNV
```

FIG. 11

| FR1 | CDR1 | FR2 |
|---|---|---|
|  | YTFT SYGIS | WVTTGPWTRDLRWMG |
| GEKPGSSVKVSCKASGYTFT | DYFMN | WMRQAPGQRLEWMG |
| QVQLQEIGPRTGEASETLSLICAVSGDSIS | SGNW*I | WVRQPPGKGLEWIG |
| QVQLQESGPGLVK*SETLSLTCTVSGGSIS | SYYWS | WIrqppGKGLEWIG |
| GYTFT | NYCMH | WVRQDHAQGLEWMG |
| QVQLQESGPGLVKpSETLSLYCAVSGDSIS | SGNW*I | WVRQPPGKGLEWIG |
| GPRLGEASETLSLTCTVSGGSIS | SSSYYw | WIRQPPGKGLEWIG |
| QVQLQESGPGLVKpSETLSLTCTVSGGSIS | SYYWS | WIRQPPGKGLEWIG |
| LSLICAVSGSSIS | SGNW*I | WVRQPPGKGLEWIG |
| SETLSLTCAVYGGSFS | GYYWS | WIRQPPGKGLEWIG |
| QVQLVQSGAEVKKPGASVKVSCKASGYTFT | NYCMH | WVRQVLAQGLEWMG |
| SETLSLICAVSGDSIS | SGNW*I | WVRQPPGKGLEWIG |
| SRAQTGEASETLSLTCTVSGGSIS | SSSYYWG | WIRQPPGKGLEWIG |
| CPLTCTVSGGSVSSGS | YYWS | WIRQPPGKGLEWIG |
| GLVKPSETLSLTCTVSGGSIS | SYYWS | WIGSPpGKGLEWIG |
| SFETLSLICAVSGDSIS | SGNW*I | WVRQPPGKGLEWIG |
| QVQLVQSGAEVKKPGSSVKVSCKASGGTFS | SYAIS | WVRQAPGQGLEWMG |
| QVQLQQWGAGLLKPSETLSLTCAVYGGSFS | GYYWS | WIRQPPGKGLEWIG |
| QLQLQESGPGLVKPSETLSLTCTVSGGSIS | SSSYYWG | WIRQPPGKGLEWIG |
| GPGLVKPSQTLSLTCTVSGGSIS | SGGYYWS | WIRQNPGKGLEWIG |

\* indicates stop codon ( unsure as sequence remains in frame)
• sequence termonates due to internal restriction site
lower case denotes frame shift

| CDR2 | FR3 | CDR3 |
|---|---|---|
| WISAYNGNTNYAQKLQG | RVTMTTDTSTSTAYMELRSLRSDDTAVYYCAR | DTVSS |
| WINAGNGNTKYSQKLQG | RVTITRDTSASTAYMQLSSLRSEDTAVYYCAR | DTVSS |
| EIHHSGSTYYNPSLKS | RITMSVDTSKNQFYLKLSS• |  |
| RIYTSGSTNYNPSLKS | RVTISVDTSKNQFSLKLSSVTAADTAVYYCAR | DTVSS |
| LVCPSDGSTSYAQKFQA | RVTITRDTSMSTAYMELSSLRSEDTAMYYCAR | DTVSS |
| EIHHSGSTYYNPSLKS | RITMSVDTSKNQFYLKLSS• |  |
| EINHSGSTNYNPSLKS | RVTISVDTSKNQFSLKLSS• |  |
| YIYYSGSTNYNPSLKS | RVTISVDTSKNQFSLKLSS• |  |
| EIHHSGSTYYNPSLKS | RITMSVDTSKNQFYLKLSS• |  |
| EINHSGSTNYNPSLKS | RVTISVDTSKNQFSLKLSSVTAADTAVYYCAR | DTVSS |
| LVCPSDGSTSYAQKFQA | RVTITRDTSMSTAYMELSSLRSEDTAMYYCAR | DTVSS |
| EIHHSGSTYYNPSLKS | RITMSVDTSKNQFYLKLSS• |  |
| SIYYSGSTYYNPSLKS | RVTIPVDTSKNQFSLKLSS• |  |
| YIYYSGSTNYNPSLKS | RVTISVDTSKNQFSLKLSSVTAADTAVYYCAR | DTVSS |
| RIYTSGSTNYNPSLKS | RVTMSVDTSKNQFSLKLSS• |  |
| EIHHSGSTYYNPSLKS | RITMSVDTSKNQFYLKLSS• |  |
| RIIPILGIANYAQKFQG | RVTITADKSTSTAYMELSSLRSEDTAVYYCAR | DTVS |
| EINHSGSTNYNPSLKS | RVTISVDTSKNQFSLKLSS• |  |
| EINHSGSTNYNPSLKS | RVTISVDTSKNQFSLKLSS• |  |
| YIYYSGSTYYNPSLKS | RVTISVDTSKNQFSLKLSSVTAADTAVYYCAR | DTVSS |

FIG. 12 pSW1

HindIII site AAGCTT

```
                                             M  K  Y  L  L  P  T  A  A
GCATGCAAATTCTATTTCAAGGAGACAGTCATAATGAAATACCTATTGCCTACGGCAGCC
        10        20        30        40        50        60
```

```
 A  G  L  L  L  A  A  Q  P  A  M  A  Q  V  Q  L  Q  E  S
GCTGGATTGTTATTACTCGCTGCCCAACCAGCGATGGCCCAGGTGCAGCTGCAGGAGTCA
        70        80        90       100       110       120
```

```
 G  P  G  L  V  A  P  S  Q  S  L  S  I  T  C  T  V  S  G  F
GGACCTGGCCTGGTGGCGCCCTCACAGAGCCTGTCCATCACATGCACCGTCTCAGGGTTC
       130       140       150       160       170       180
```

```
 S  L  T  G  Y  G  V  N  W  V  R  Q  P  P  G  K  G  L  E  W
TCATTAACCGGCTATGGTGTAAACTGGGTTCGCCAGCCTCCAGGAAAGGGTCTGGAGTGG
       190       200       210       220       230       240
```

```
 L  G  M  I  W  G  D  G  N  T  D  Y  N  S  A  L  K  S  R  L
CTGGGAATGATTTGGGGTGATGGAAACACAGACTATAATTCAGCTCTCAAATCCAGACTG
       250       260       270       280       290       300
```

```
 S  I  S  K  D  N  S  K  S  Q  V  F  L  K  M  N  S  L  H  T
AGCATCAGCAAGGACAACTCCAAGAGCCAAGTTTTCTTAAAAATGAACAGTCTGCACACT
       310       320       330       340       350       360
```

```
 D  D  T  A  R  Y  Y  C  A  R  E  R  D  Y  R  L  D  Y  W  G
GATGACACAGCCAGGTACTACTGTGCCAGAGAGAGAGATTATAGGCTTGACTACTGGGGC
       370       380       390       400       410       420
```

```
 Q  G  T  T  V  T  V  S  S                  SmaI
CAAGGCACCACGGTCACCGTCTCCTCATAATAAGAGCTATCCCGGGCTAAGCTCGAATTC
       430       440       450       460       470       480
```

FIG. 13 pSW2

HindIII AAGCTT

```
                                          M  K  Y  L  L  P  T  A  A
GCATGCAAATTCTATTTCAAGGAGACAGTCATAATGAAATACCTATTGCCTACGGCAGCC
        10        20        30        40        50        60

A  G  L  L  L  L  A  A  Q  P  A  M  A  Q  V  Q  L  Q  E  S
GCTGGATTGTTATTACTCGCTGCCCAACCAGCGATGGCCCAGGTGCAGCTGCAGGAGTCA
        70        80        90       100       110       120

G  P  G  L  V  A  P  S  Q  S  L  S  I  T  C  T  V  S  G  F
GGACCTGGCCTGGTGGCGCCCTCACAGAGCCTGTCCATCACATGCACCGTCTCAGGGTTC
       130       140       150       160       170       180

S  L  T  G  Y  G  V  N  W  V  R  Q  P  P  G  K  G  L  E  W
TCATTAACCGGCTATGGTGTAAACTGGGTTCGCCAGCCTCCAGGAAAGGGTCTGGAGTGG
       190       200       210       220       230       240

L  G  M  I  W  G  D  G  N  T  D  Y  N  S  A  L  K  S  R  L
CTGGGAATGATTTGGGGTGATGGAAACACAGACTATAATTCAGCTCTCAAATCCAGACTG
       250       260       270       280       290       300

S  I  S  K  D  N  S  K  S  Q  V  F  L  K  M  N  S  L  H  T
AGCATCAGCAAGGACAACTCCAAGAGCCAAGTTTTCTTAAAAATGAACAGTCTGCACACT
       310       320       330       340       350       360

D  D  T  A  R  Y  Y  C  A  R  E  R  D  Y  R  L  D  Y  W  G
GATGACACAGCCAGGTACTACTGTGCCAGAGAGAGAGATTATAGGCTTGACTACTGGGGC
       370       380       390       400       410       420

Q  G  T  T  V  T  V  S  S
CAAGGCACCACGGTCACCGTCTCCTCATAATAAGAGCTCGAATTCGCCAAGCTTGCATGC
       430       440       450       460       470       480

M  K  Y  L  L  P  T  A  A  A  G
AAATTCTATTTCAAGGAGACAGTCATAATGAAATACCTATTGCCTACGGCAGCCGCTGGA
       490       500       510       520       530       540

L  L  L  L  A  A  Q  P  A  M  A  D  I  V  L  T  Q  S  P  A
TTGTTATTACTCGCTGCCCAACCAGCGATGGCCGACATCGTCCTGACTCAGTCTCCAGCC
       550       560       570       580       590       600

S  L  S  A  S  V  G  E  T  V  T  I  T  C  R  A  S  G  N  I
TCCCTTTCTGCGTCTGTGGGAGAAACTGTCACCATCACATGTCGAGCAAGTGGGAATATT
       610       620       630       640       650       660

H  N  Y  L  A  W  Y  Q  Q  K  Q  G  K  S  P  Q  L  L  V  Y
CACAATTATTTAGCATGGTATCAGCAGAAACAGGGAAAATCTCCTCAGCTCCTGGTCTAT
       670       680       690       700       710       720
```

FIG. 14a

```
Y  T  T  T  L  A  D  G  V  P  S  R  F  S  G  S  G  S  G  T
TATACAACAACCTTAGCAGATGGTGTGCCATCAAGGTTCAGTGGCAGTGGATCAGGAACA
    730       740       750       760       770       780

Q  Y  S  L  K  I  N  S  L  Q  P  E  D  F  G  S  Y  Y  C  Q
CAATATTCTCTCAAGATCAACAGCCTGCAACCTGAAGATTTTGGGAGTTATTACTGTCAA
    790       800       810       820       830       840

H  F  W  S  T  P  R  T  F  G  G  G  T  K  L  E  I  K  R
CATTTTTGGAGTACTCCTCGGACGTTCGGTGGAGGCACCAAGCTGGAAATCAAACGGTAA
    850       860       870       880       890       900

TAAGAGCTCGAATTC
    910
```

FIG. 14 b

```
pSW1HPOLYMYC

HindIII site AAGCTT

M  K  Y  L  L  P  T  A  A
GCATGCAAATTCTATTTCAAGGAGACAGTCATAATGAAATACCTATTGCCTACGGCAGCC
    10        20        30        40        50        60

A  G  L  L  L  L  A  A  Q  P  A  M  A  Q  V  Q  L  Q
GCTGGATTGTTATTACTCGCTGCCCAACCAGCGATGGCCCAGGTGCAGCTGCAG
    70        80        90        100       110  PstI

Polylinker
TCTAGA   GTCGAC   CTCGAG
 XbaI     SalI     XhoI

MYC PEPTIDE
    V  T  V  S  S  E  Q  K  L  I  S  E  E  D  L  N  *  *
GGTCACCGTCTCCTCAGAACAAAAACTCATCTCAGAAGAGGATCTGAATTAATAA
BstEII

GGGCTAAGCTCGAATTC
```

FIG. 15 pSW2HPOLY

HindIII AAGCTT

```
                                              M  K  Y  L  L  P  T  A  A
GCATGCAAATTCTATTTCAAGGAGACAGTCATAATGAAATACCTATTGCCTACGGCAGCC
         10        20        30        40        50        60
```

```
 A  G  L  L  L  L  A  A  Q  P  A  M  A  Q  V  Q  L  Q
GCTGGATTGTTATTACTCGCTGCCCAACCAGCGATGGCCCAGGTGCAGCTGCAG
         70        80        90       100       110 PstI
```

TCTAGA  GTCGAC  CTCGAG
 XbaI    SalI    XhoI

```
 V  T  V  S  S
GGTCACCGTCTCCTCATAATAAGAGCTCGAATTCGCCAAGCTTGCATGC
BstEII 430       440       450       460       470       480
```

```
                                              M  K  Y  L  L  P  T  A  A  A  G
AAATTCTATTTCAAGGAGACAGTCATAATGAAATACCTATTGCCTACGGCAGCCGCTGGA
        490       500       510       520       530       540
```

```
 L  L  L  A  A  Q  P  A  M  A  D  I  V  L  T  Q  S  P  A
TTGTTATTACTCGCTGCCCAACCAGCGATGGCCGACATCGTCCTGACTCAGTCTCCAGCC
        550       560       570       580       590       600
```

```
 S  L  S  A  S  V  G  E  T  V  T  I  T  C  R  A  S  G  N  I
TCCCTTTCTGCGTCTGTGGGAGAAACTGTCACCATCACATGTCGAGCAAGTGGGAATATT
        610       620       630       640       650       660
```

```
 H  N  Y  L  A  W  Y  Q  Q  K  Q  G  K  S  P  Q  L  L  V  Y
CACAATTATTTAGCATGGTATCAGCAGAAACAGGGAAAATCTCCTCAGCTCCTGGTCTAT
        670       680       690       700       710       720
```

```
 Y  T  T  T  L  A  D  G  V  P  S  R  F  S  G  S  G  S  G  T
TATACAACAACCTTAGCAGATGGTGTGCCATCAAGGTTCAGTGGCAGTGGATCAGGAACA
        730       740       750       760       770       780
```

```
 Q  Y  S  L  K  I  N  S  L  Q  P  E  D  F  G  S  Y  Y  C  Q
CAATATTCTCTCAAGATCAACAGCCTGCAACCTGAAGATTTTGGGAGTTATTACTGTCAA
        790       800       810       820       830       840
```

```
 H  F  W  S  T  P  R  T  F  G  G  G  T  K  L  E  I  K  R
CATTTTTGGAGTACTCCTCGGACGTTCGGTGGAGGCACCAAGCTGGAAATCAAACGGTAA
        850       860       870       880       890       900
```

```
TAAGAGCTCGAATTC
        910
```

FIG. 19

```
                                              M  K  Y  L  L  P  T
AAGCTTGCATGCAAATTCTATTTCAAGGAGACAGTCATAATGAAATACCTATTGCCTACG
        10        20        30        40        50        60

A  A  A  G  L  L  L  L  A  A  Q  P  A  M  A  Q  V  Q  L  Q
GCAGCCGCTGGATTGTTATTACTCGCTGCCCAACCAGCGATGGCCCAGGTGCAGCTGCAG
        70        80        90       100       110       120

E  S  G  P  G  L  V  A  P  S  Q  S  L  S  I  T  C  T  V  S
GAGTCAGGACCTGGCCTGGTGGCGCCCTCACAGAGCCTGTCCATCACATGCACCGTCTCA
       130       140       150       160       170       180

G  F  S  L  T  G  Y  G  V  N  W  V  R  Q  P  P  G  K  G  L
GGGTTCTCATTAACCGGCTATGGTGTAAACTGGGTTCGCCAGCCTCCAGGAAAGGGTCTG
       190       200       210       220       230       240

E  W  L  G  M  I  W  G  D  G  N  T  D  Y  N  S  A  L  K  S
GAGTGGCTGGGAATGATTTGGGGTGATGGAAACACAGACTATAATTCAGCTCTCAAATCC
       250       260       270       280       290       300

R  L  S  I  S  K  D  N  S  K  S  Q  V  F  L  K  M  N  S  L
AGACTGAGCATCAGCAAGGACAACTCCAAGAGCCAAGTTTTCTTAAAAATGAACAGTCTG
       310       320       330       340       350       360

H  T  D  D  T  A  R  Y  Y  C  A  R  E  R  D  Y  R  L  D  Y
CACACTGATGACACAGCCAGGTACTACTGTGCCAGAGAGAGAGATTATAGGCTTGACTAC
       370       380       390       400       410       420

W  G  Q  G  T  T  V  T  V  S  S  G  G  A  P  A  A  A  P
TGGGGCCAAGGCACCACGGTCACCGTCTCCTCAGGTGGTGGTGCTCCAGCAGCTGCACCT
       430       440       450       460       470       480

A  G  G  G  Q  V  Q  L  K  E  S  G  P  G  L  V  A  P  S  Q
GCTGGAGGAGGACAGGTGCAGCTGAAGGAGTCAGGACCTGGCCTGGTGGCGCCCTCACAG
       490       500       510       520       530       540

S  L  S  I  T  C  T  V  S  G  F  S  L  T  G  Y  G  V  N  W
AGCCTGTCCATCACATGCACCGTCTCAGGGTTCTCATTAACCGGCTATGGTGTAAACTGG
       550       560       570       580       590       600

V  R  Q  P  P  G  K  G  L  E  W  L  G  M  I  W  G  D  G  N
GTTCGCCAGCCTCCAGGAAAGGGTCTGGAGTGGCTGGGAATGATTTGGGGTGATGGAAAC
       610       620       630       640       650       660

T  D  Y  N  S  A  L  K  S  R  L  S  I  S  K  D  N  S  K  S
ACAGACTATAATTCAGCTCTCAAATCCAGACTGAGCATCAGCAAGGACAACTCCAAGAGC
       670       680       690       700       710       720

Q  V  F  L  K  M  N  S  L  H  T  D  D  T  A  R  Y  Y  C  A
CAAGTTTTCTTAAAAATGAACAGTCTGCACACTGATGACACAGCCAGGTACTACTGTGCC
       730       740       750       760       770       780

R  E  R  D  Y  R  L  D  Y  W  G  Q  G  T  T  V  T  V  S  S
AGAGAGAGAGATTATAGGCTTGACTACTGGGGCCAAGGCACCACGGTCACCGTCTCCTCA
       790       800       810       820       830       840
 *  *
TAATAAGAGCTC
   850
```

FIG. 20

```
                                              M  K  Y  L  L  P  T  A  A
GCATGCAAATTCTATTTCAAGGAGACAGTCATAATGAAATACCTATTGCCTACGGCAGCC
         10        20        30        40        50        60

A  G  L  L  L  L  A  A  Q  P  A  M  A  Q  V  Q  L  Q  E  S
GCTGGATTGTTATTACTCGCTGCCCAACCAGCGATGGCCCAGGTGCAGCTGCAGGAGTCA
         70        80        90       100       110       120

G  P  G  L  V  A  P  S  Q  S  L  S  I  T  C  T  V  S  G  F
GGACCTGGCCTGGTGGCGCCCTCACAGAGCCTGTCCATCACATGCACCGTCTCAGGGTTC
        130       140       150       160       170       180

S  L  T  G  Y  G  V  N  W  V  R  Q  P  P  G  K  G  L  E  W
TCATTAACCGGCTATGGTGTAAACTGGGTTCGCCAGCCTCCAGGAAAGGGTCTGGAGTGG
        190       200       210       220       230       240

L  G  M  I  W  G  D  G  N  T  D  Y  N  S  A  L  K  S  R  L
CTGGGAATGATTTGGGGTGATGGAAACACAGACTATAATTCAGCTCTCAAATCCAGACTG
        250       260       270       280       290       300

S  I  S  K  D  N  S  K  S  Q  V  F  L  K  M  N  S  L  H  T
AGCATCAGCAAGGACAACTCCAAGAGCCAAGTTTTCTTAAAAATGAACAGTCTGCACACT
        310       320       330       340       350       360

D  D  T  A  R  Y  Y  C  A  R  E  R  D  Y  R  L  D  Y  W  G
GATGACACAGCCAGGTACTACTGTGCCAGAGAGAGAGATTATAGGCTTGACTACTGGGGC
        370       380       390       400       410       420

Q  G  T  T  V  T  V  S  S  R  T  P  E  M  P  V  L  E  N  R
CAAGGCACCACGGTCACCGTCTCCTCACGGACACCAGAAATGCCTGTTCTGGAAAACCGG
        430       440       450       460       470       480

A  A  Q  G  D  I  T  A  P  G  G  A  R  R  L  T  G  D  Q  T
GCTGCTCAGGGCGATATTACTGCACCCGGCGGTGCTCGCCGTTTAACGGGTGATCAGACT
        490       500       510       520       530       540

A  A  L  R  D  S  L  S  D  K  P  A  K  N  I  I  L  L  I  G
GCCGCTCTGCGTGATTCTCTTAGCGATAAACCTGCAAAAAATATTATTTTGCTGATTGGC
        550       560       570       580       590       600

D  G  M  G  D  S  E  I  T  A  A  R  N  Y  A  E  G  A  G  G
GATGGGATGGGGGACTCGGAAATTACTGCCGCACGTAATTATGCCGAAGGTGCGGGCGGC
        610       620       630       640       650       660

F  F  K  G  I  D  A  L  P  L  T  G  Q  Y  T  H  Y  A  L  N
TTTTTTAAAGGTATAGATGCCTTACCGCTTACCGGGCAATACACTCACTATGCGCTGAAT
        670       680       690       700       710       720

K  K  T  G  K  P  D  Y  V  T  D  S  A  A  S  A  T  A  W  S
AAAAAAACCGGCAAACCGGACTACGTCACCGACTCGGCTGCATCAGCAACCGCCTGGTCA
        730       740       750       760       770       780
```

FIG. 21a

```
      T  G  V  K  T  Y  N  G  A  L  G  V  D  I  H  E  K  D  H  P
   ACCGGTGTCAAAACCTATAACGGCGCGCTGGGCGTCGATATTCACGAAAAAGATCACCCA
        790       800       810       820       830       840

T  I  L  E  M  A  K  A  A  G  L  A  T  G  N  V  S  T  A  E
   ACGATTCTGGAAATGGCAAAAGCCGCAGGTCTGGCGACCGGTAACGTTTCTACCGCAGAG
        850       860       870       880       890       900

L  Q  D  A  T  P  A  A  L  V  A  H  V  T  S  R  K  C  Y  G
   TTGCAGGATGCCACGCCCGCTGCGCTGGTGGCACATGTGACCTCGCGCAAATGCTACGGT
        910       920       930       940       950       960

P  S  A  T  S  E  K  C  P  G  N  A  L  E  K  G  G  K  G  S
   CCGAGCGCGACCAGTGAAAAATGTCCGGGTAACGCTCTGGAAAAAGGCGGAAAAGGATCG
        970       980       990      1000      1010      1020

I  T  E  Q  L  L  N  A  R  A  D  V  T  L  G  G  A  K  T
   ATTACCGAACAGCTGCTTAACGCTCGTGCCGACGTTACGCTTGGCGGCGGCGCAAAAACC
       1030      1040      1050      1060      1070      1080

F  A  E  T  A  T  A  G  E  W  Q  G  K  T  L  R  E  Q  A  Q
   TTTGCTGAAACGGCAACCGCTGGTGAATGGCAGGGAAAAACGCTGCGTGAACAGGCACAG
       1090      1100      1110      1120      1130      1140

A  R  G  Y  Q  L  V  S  D  A  A  S  L  N  S  V  T  E  A  N
   GCGCGTGGTTATCAGTTGGTGAGCGATGCTGCCTCACTGAATTCGGTGACGGAAGCGAAT
       1150      1160      1170      1180      1190      1200

Q  Q  K  P  L  L  G  L  F  A  D  G  N  M  P  V  R  W  L  G
   CAGCAAAAACCCCTGCTTGGCCTGTTTGCTGACGGCAATATGCCAGTGCGCTGGCTAGGA
       1210      1220      1230      1240      1250      1260

P  K  A  T  Y  H  G  N  I  D  K  P  A  V  T  C  T  P  N  P
   CCGAAAGCAACGTACCATGGCAATATCGATAAGCCCGCAGTCACCTGTACGCCAAATCCG
       1270      1280      1290      1300      1310      1320

Q  R  N  D  S  V  P  T  L  A  Q  M  T  D  K  A  I  E  L  L
   CAACGTAATGACAGTGTACCAACCCTGGCGCAGATGACCGACAAAGCCATTGAATTGTTG
       1330      1340      1350      1360      1370      1380

S  K  N  E  K  G  F  F  L  Q  V  E  G  A  S  I  D  K  Q  D
   AGTAAAAATGAGAAAGGCTTTTTCCTGCAAGTTGAAGGTGCGTCAATCGATAAACAGGAT
       1390      1400      1410      1420      1430      1440

H  A  A  N  P  C  G  Q  I  G  E  T  V  D  L  D  E  A  V  Q
   CATGCTGCGAATCCTTGTGGGCAAATTGGCGAGACGGTCGATCTCGATGAAGCCGTACAA
       1450      1460      1470      1480      1490      1500

R  A  L  E  F  A  K  K  E  G  N  T  L  V  I  V  T  A  D  H
   CGGGCGCTGGAATTCGCTAAAAAGGAGGGTAACACGCTGGTCATAGTCACCGCTGATCAC
       1510      1520      1530      1540      1550      1560
```

FIG. 21b

```
     A   H   A   S   Q   I   V   A   P   D   T   K   A   P   G   L   T   Q   A   L
    GCCCACGCCAGCCAGATTGTTGCGCCGGATACCAAAGCTCCGGGCCTCACCCAGGCGCTA
        1570      1580      1590      1600      1610      1620

N   T   K   D   G   A   V   M   V   M   S   Y   G   N   S   E   E   D   S   Q
    AATACCAAAGATGGCGCAGTGATGGTGATGAGTTACGGGAACTCCGAAGAGGATTCACAA
        1630      1640      1650      1660      1670      1680

E   H   T   G   S   Q   L   R   I   A   A   Y   G   P   H   A   A   N   V   V
    GAACATACCGGCAGTCAGTTGCGTATTGCGGCGTATGGCCCGCATGCCGCCAATGTTGTT
        1690      1700      1710      1720      1730      1740

G   L   T   D   Q   T   D   L   F   Y   T   M   K   A   A   L   G   L   K   *
    GGACTGACCGACCAGACCGATCTCTTCTACACCATGAAAGCCGCTCTGGGGCTGAAATAA
        1750      1760      1770      1780      1790      1800

AACCGCGCCCGGGAGTGAATTTTCGCTGCCGGGTGGTTTTTTTGCTGTTAGC
        1810      1820      1830      1840      1850
```

FIG. 21c

```
                                              M  K  Y  L  L  P  T  A  A
GCATGCAAATTCTATTTCAAGGAGACAGTCATAATGAAATACCTATTGCCTACGGCAGCC
    10        20        30        40        50        60

A  G  L  L  L  L  A  A  Q  P  A  M  A  Q  V  Q  L  Q  E  S
GCTGGATTGTTATTACTCGCTGCCCAACCAGCGATGGCCCAGGTGCAGCTGCAGGAGTCA
    70        80        90       100       110       120

G  P  G  L  V  A  P  S  Q  S  L  S  I  T  C  T  V  S  G  F
GGACCTGGCCTGGTGGCGCCCTCACAGAGCCTGTCCATCACATGCACCGTCTCAGGGTTC
   130       140       150       160       170       180

S  L  T  G  Y  G  V  N  W  V  R  Q  P  P  G  K  G  L  E  W
TCATTAACCGGCTATGGTGTAAACTGGGTTCGCCAGCCTCCAGGAAAGGGTCTGGAGTGG
   190       200       210       220       230       240

L  G  M  I  W  G  D  G  N  T  D  Y  N  S  A  L  K  S  R  L
CTGGGAATGATTTGGGGTGATGGAAACACAGACTATAATTCAGCTCTCAAATCCAGACTG
   250       260       270       280       290       300

S  I  S  K  D  N  S  K  S  Q  V  F  L  K  M  N  S  L  H  T
AGCATCAGCAAGGACAACTCCAAGAGCCAAGTTTTCTTAAAAATGAACAGTCTGCACACT
   310       320       330       340       350       360

D  D  T  A  R  Y  Y  C  A  R  E  R  D  Y  R  L  D  Y  W  G
GATGACACAGCCAGGTACTACTGTGCCAGAGAGAGAGATTATAGGCTTGACTACTGGGGC
   370       380       390       400       410       420

Q  G  T  T  V  T  V  S  S  *  *
CAAGGCACCACGGTCACCGTCTCCTCATAATAAGAGCTATCCCGGGAGCTTGCATGCAAA
   430       440       450       460       470       480

M  K  Y  L  L  P  T  A  A  A  G  L
TTCTATTTCAAGGAGACAGTCATAATGAAATACCTATTGCCTACGGCAGCCGCTGGATTG
   490       500       510       520       530       540

L  L  A  A  Q  P  A  M  A  D  I  E  L  V  D  L  E  I  K
TTATTACTCGCTGCCCAACCAGCGATGGCCGACATCGAGCTCGTCGACCTCGAGATCAAA
   550       560       570       580       590       600

R  E  Q  K  L  I  S  E  E  D  L  N  *  *
CGGGAACAAAAACTCATCTCAGAAGAGGATCTGAATTAATAATGATCAAACGGTAATAAG
   610       620       630       640       650       660

GATCCAGCTCGAATTC
   670
```

FIG. 22

```
                                         A
Q   V   Q   L   Q   E   S   G   P   G   L   V   Q   P   S   Q   S   L   S   I
CAGGTGCAGCTGCAGGAGTCAGGACCTGGCCTAGTGCAGCCCTCACAGAGCCTGTCCATC
       10          20          30          40          50          60

G               N               P
T   C   T   V   S   G   F   S   L   T   S   Y   G   V   H   W   V   R   Q   S
ACCTGCACAGTCTCTGGTTTCTCATTAACTAGCTATGGTGTACACTGGGTTCGCCAGTCT
                                                                          C
       70          80          90         100         110         120

P   G   K   G   L   E   W   L   G   M   I   W   G   D   G   N   T   D   Y   N
CCAGGAAAGGGTCTGGAGTGGCTGGGAATGATTTGGGGTGATGGAAACACAGACTATAAT
      130         140         150         160         170         180

S   A   L   K   S   R   L   S   I   S   K   D   N   S   K   S   Q   V   F   L
TCAGCTCTCAAATCCAGACTGAGCATCAGCAAGGACAACTCCAAGAGCCAAGTTTTCTTA
      190         200         210         220         230         240

K   M   N   S   L   H   T   D   D   T   A   R   Y   Y   C   A   R   E   R   D
AAAATGAACAGTCTGCACACTGATGACACAGCCAGGTACTACTGTGCCAGAGAGAGAGAT
      250         260         270         280         290         300

Y   R   L   D   Y   W   G   Q   G   T   T   V   T   V   S   S
TATAGGCTTGACTACTGGGGCCAAGGGACCACGGTCACCGTCTCCTCA
      310         320         330         340
```

FIG. 23

SINGLE DOMAIN LIGANDS, RECEPTORS COMPRISING SAID LIGANDS, METHODS FOR THEIR PRODUCTION, AND USE OF SAID LIGANDS AND RECEPTORS

This is a continuation of application Ser. No. 09/722,364, filed Nov. 28, 2000, now U.S. Pat. No. 6,545,142, which is a continuation of Ser. No. 08/470,031, filed Jun. 6, 1995, which issued as U.S. Pat. No. 6,248,516 on Jun. 19, 2001, which is a divisional of Ser. No. 08/332,046, filed Nov. 1, 1994 now abandoned; which is a continuation of Ser. No. 07/796,805, filed Nov. 25, 1991 now abandoned, which is a divisional of Ser. No. 07/580,374, filed Sep. 11, 1990, abandoned the entire contents of each of which is hereby incorporate by references in this application.

The present invention relates to single domain ligands derived from molecules in the immunoglobulin (Ig) superfamily, receptors comprising at least one such ligand, methods for cloning, amplifying and expressing DNA sequences encoding such ligands, methods for the use of said DNA sequences in the production of Ig-type molecules and said ligands or receptors, and the use of said ligands or receptors in therapy, diagnosis or catalysis.

A list of references is appended to the end of the description. The documents listed therein are referred to in the description by number, which is given in square brackets [ ].

The Ig superfamily includes not only the Igs themselves but also such molecules as receptors on lymphoid cells such as T lymphocytes. Immunoglobulins comprise at least one heavy and one light chain covalently bonded together. Each chain is divided into a number of domains. At the N terminal end of each chain is a variable domain. The variable domains on the heavy and light chains fit together to form a binding site designed to receive a particular target molecule. In the case of Igs, the target molecules are antigens. T-cell receptors have two chains of equal size, the α and β chains, each consisting of two domains. At the N-terminal end of each chain is a variable domain and the variable domains on the α and β chains are believed to fit together to form a binding site for target molecules, in this case peptides presented by a histocompatibility antigen. The variable domains are so called because their amino acid sequences vary particularly from one molecule to another. This variation in sequence enables the molecules to recognise an extremely wide variety of target molecules.

Much research has been carried out on Ig molecules to determine how the variable domains are produced. It has been shown that each variable domain comprises a number of areas of relatively conserved sequence and three areas of hypervariable sequence. The three hypervariable areas are generally known as complementarity determining regions (CDRs).

Crystallographic studies have shown that in each variable domain of an Ig molecule the CDRs are supported on framework areas formed by the areas of conserved sequences. The three CDRs are brought together by the framework areas and, together with the CDRs on the other chain, form a pocket in which the target molecule is received.

Since the advent of recombinant DNA technology, there has been much interest in the use of such technology to clone and express Ig molecules and derivatives thereof. This interest is reflected in the numbers of patent applications and other publications on the subject.

The earliest work on the cloning and expression of full Igs in the patent literature is EP-A-0 120 694 (Boss). The Boss application also relates to the cloning and expression of chimeric antibodies. Chimeric antibodies are Ig-type molecules in which the variable domains from one Ig are fused to constant domains from another Ig. Usually, the variable domains are derived from an Ig from one species (often a mouse Ig) and the constant domains are derived from an Ig from a different species (often a human Ig).

A later European patent application, EP-A-0 125 023 (Genentech), relates to much the same subject as the Boss application, but also relates to the production by recombinant DNA technology of other variations of Ig-type molecules.

EP-A-0 194 276 (Neuberger) discloses not only chimeric antibodies of the type disclosed in the Boss application but also chimeric antibodies in which some or all of the constant domains have been replaced by non-Ig derived protein sequences. For instance, the heavy chain CH2 and CH3 domains may be replaced by protein sequences derived from an enzyme or a protein toxin.

EP-A-0 239 400 (Winter) discloses a different approach to the production of Ig molecules. In this approach, only the CDRs from a first type of Ig are grafted onto a second type of Ig in place of its normal CDRs. The Ig molecule thus produced is predominantly of the second type, since the CDRs form a relatively small part of the whole Ig. However, since the CDRs are the parts which define the specificity of the Ig, the Ig molecule thus produced has its specificity derived from the first Ig.

Hereinafter, chimeric antibodies, CDR-grafted Igs, the altered antibodies described by Genentech, and fragments, of such Igs such as F(ab')$_2$ and Fv fragments are referred to herein as modified antibodies.

One of the main reasons for all the activity in the Ig field using recombinant DNA technology is the desire to use Igs in therapy. It is well known that, using the hybridoma technique developed by Kohler and Milstein, it is possible to produce monoclonal antibodies (MAbs) of almost any specificity. Thus, MAbs directed against cancer antigens have been produced. It is envisaged that these MAbs could be covalently attached or fused to toxins to provide "magic bullets" for use in cancer therapy. MAbs directed against normal tissue or cell surface antigens have also been produced. Labels can be attached to these so that they can be used for in vivo imaging.

The major obstacle to the use of such MAbs in therapy or in vivo diagnosis is that the vast majority of MAbs which are produced are of rodent, in particular mouse, origin. It is very difficult to produce human MAbs. Since most MAbs are derived from non-human species, they are antigenic in humans. Thus, administration of these MAbs to humans generally results in an anti-Ig response being mounted by the human. Such a response can interfere with therapy or diagnosis, for instance by destroying or clearing the antibody quickly, or can cause allergic reactions or immune complex hypersensitivity which has adverse effects on the patient.

The production of modified Igs has been proposed to ensure that the Ig administered to a patient is as "human" as possible, but still retains the appropriate specificity. It is therefore expected that modified Igs will be as effective as the MAb from which the specificity is derived but at the same time not very antigenic. Thus, it should be possible to use the modified Ig a reasonable number of times in a treatment or diagnosis regime.

At the level of the gene, it is known that heavy chain variable domains are encoded by a "rearranged" gene which is built from three gene segments: an "unrearranged" VH gene (encoding the N-terminal three framework regions, first two complete CDRs and the first part of the third CDR), a diversity (DH)-segment (DH) (encoding the central portion of the third CDR) and a joining segment (JH) (encoding the last part of the third CDR and the fourth framework region). In the maturation of B-cells, the genes rearrange so that each unrearranged VH gene is linked to one DH gene and one JH gene. The rearranged gene corresponds to VH-DH-JH. This rearranged gene is linked to a gene which encodes the constant portion of the Ig chain.

For light chains, the situation is similar, except that for light chains there is no diversity region. Thus light chain variable domains are encoded by an "unrearranged" VL gene and a JL gene. There are two types of light chains, kappa (κ) or lambda (λ), which are built respectively from unrearranged Vκ genes and Jκ segments, and from unrearranged Vλ genes and Jλ segments.

Previous work has shown that it is necessary to have two variable domains in association together for efficient binding. For example, the associated heavy and light chain variable domains were shown to contain the antigen binding site [1]. This assumption is borne out by X-ray crystallographic studies of crystallised antibody/antigen complexes [2-6] which show that both the heavy and light chains of the antibody's variable domains contact the antigen. The expectation that association of heavy and light chain variable domains is necessary for efficient antigen binding underlies work to co-secrete these domains from bacteria [1], and to link the domains together by a short section of polypeptide as in the single chain antibodies [8, 9].

Binding of isolated heavy and light chains had also been detected. However the evidence suggested strongly that this was a property of heavy or light chain dimers. Early work, mainly with polyclonal antibodies, in which antibody heavy and light chains had been separated under denaturing conditions [10] suggested that isolated antibody heavy chains could bind to protein antigens [11] or hapten [12]. The binding of protein antigen was not characterised, but the hapten-binding affinity of the heavy chain fragments was reduced by two orders of magnitude [12] and the number of hapten molecules binding were variously estimated as 0.14 or 0.37 [13] or 0.26 [14] per isolated heavy chain. Furthermore binding of haptens was shown to be a property of dimeric heavy or dimeric light chains [14]. Indeed light chain dimers have been crystallised. It has been shown that in light chain dimers the two chains form a cavity which is able to bind to a single molecule of hapten [15].

This confirms the assumption that, in order to obtain efficient binding, it is necessary to have a dimer, and preferably a heavy chain/light chain dimer, containing the respective variable domains. This assumption also underlies the teaching of the patent references cited above, wherein the intention is always to produce dimeric, and preferably heavy/light chain dimeric, molecules.

It has now been discovered, contrary to expectations, that isolated Ig heavy chain variable domains can bind to antigen in a 1:1 ratio and with binding constants of equivalent magnitude to those of complete antibody molecules. In view of what was known up until now and in view of the assumptions made by those skilled in the art, this is highly surprising.

Therefore, according to a first aspect of the present invention, there is provided a single domain ligand consisting at least part of the variable domain of one chain of a molecule from the Ig superfamily.

Preferably, the ligand consists of the variable domain of an Ig light, or, most preferably, heavy chain.

The ligand may be produced by any known technique, for instance by controlled cleavage of Ig superfamily molecules or by peptide synthesis. However, preferably the ligand is produced by recombinant DNA technology. For instance, the gene encoding the rearranged gene for a heavy chain variable domain may be produced, for instance by cloning or gene synthesis, and placed into a suitable expression vector. The expression vector is then used to transform a compatible host cell which is then cultured to allow the ligand to be expressed and, preferably, secreted.

If desired, the gene for the ligand can be mutated to improve the properties of the expressed domain, for example to increase the yields of expression or the solubility of the ligand, to enable the ligand to bind better, or to introduce a second site for covalent attachment (by introducing chemically reactive residues such as cysteine and histidine) or non-covalent binding of other molecules. In particular it would be desirable to introduce a second site for binding to serum components, to prolong the residence time of the domains in the serum; or for binding to molecules with effector functions, such as components of complement, or receptors on the surfaces of cells.

Thus, hydrophobic residues which would normally be at the interface of the heavy chain variable domain with the light chain variable domain could be mutated to more hydrophilic residues to improve solubility; residues in the CDR loops could be mutated to improve antigen binding; residues on the other loops or parts of the β-sheet could be mutated to introduce new binding activities. Mutations could include single point mutations, multiple point mutations or more extensive changes and could be introduced by any of a variety of recombinant DNA methods, for example gene synthesis, site directed mutagenesis or the polymerase chain reaction.

Since the ligands of the present invention have equivalent binding affinity to that of complete Ig molecules, the ligands can be used in many of the ways as are Ig molecules or fragments. For example, Ig molecules have been used in therapy (such as in treating cancer, bacterial and viral diseases), in diagnosis (such as pregnancy testing), in vaccination (such as in producing anti-idiotypic antibodies which mimic antigens), in modulation of activities of hormones or growth factors, in detection, in biosensors and in catalysis.

It is envisaged that the small size of the ligands of the present invention may confer some advantages over complete antibodies, for example, in neutralising the activity of low molecular weight drugs (such as digoxin) and allowing their filtration from the kidneys with drug attached; in penetrating tissues and tumours; in neutralising viruses by binding to small conserved regions on the surfaces of viruses such as the "canyon" sites of viruses [16]; in high resolution epitope mapping of proteins; and in vaccination by ligands which mimic antigens.

The present invention also provides receptors comprising a ligand according to the first aspect of the invention linked to one or more of an effector molecule, a label, a surface, or one or more other ligands having the same or different specificity.

A receptor comprising a ligand linked to an effector molecule may be of use in therapy. The effector molecule may be a toxin, such as ricin or pseudomonas exotoxin, an enzyme which is able to activate a prodrug, a binding partner or a radio-isotope. The radio-isotope may be directly linked to the ligand or may be attached thereto by a chelating structure which is directly linked to the ligand. Such ligands with attached isotopes are much smaller than those based on Fv fragments, and could penetrate tissues and access tumours more readily.

A receptor comprising a ligand linked to a label may be of use in diagnosis. The label may be a heavy metal atom or a radio-isotope, in which case the receptor can be used for in vivo imaging using X-ray or other scanning apparatus. The metal atom or radio-isotope may be attached to the ligand either directly or via a chelating structure directly linked to the ligand. For in vitro diagnostic testing, the label may be a heavy metal atom, a radio-isotope, an enzyme, a fluorescent or coloured molecule or a protein or peptide tag which can be detected by an antibody, an antibody fragment or another protein. Such receptors would be used in any of the known diagnostic tests, such as ELISA or fluorescence-linked assays.

A receptor comprising a ligand linked to a surface, such as a chromatography medium, could be used for purification of other molecules by affinity chromatography. Linking of ligands to cells, for example to the outer membrane proteins of E. coli or to hydrophobic tails which localise the ligands in the cell membranes, could allow a simple diagnostic test in which the bacteria or cells would agglutinate in the presence of molecules bearing multiple sites for binding the ligand(s).

Receptors comprising at least two ligands can be used, for instance, in diagnostic tests. The first ligand will bind to a test antigen and the second ligand will bind to a reporter molecule, such as an enzyme, a fluorescent dye, a coloured dye, a radio-isotope or a coloured-, fluorescently- or radio-labelled protein.

Alternatively, such receptors may be useful in increasing the binding to an antigen. The first ligand will bind to a first epitope of the antigen and the second ligand will bind to a second epitope. Such receptors may also be used for increasing the affinity and specificity of binding to different antigens in close proximity on the surface of cells. The first ligand will bind to the first antigen and the second epitope to the second antigen: strong binding will depend on the co-expression of the epitopes on the surface of the cell. This may be useful in therapy of tumours, which can have elevated expression of several surface markers. Further ligands could be added to further improve binding or specificity. Moreover, the use of strings of ligands, with the same or multiple specificities, creates a larger molecule which is less readily filtered from the circulation by the kidney.

For vaccination with ligands which mimic antigens, the use of strings of ligands may prove more effective than single ligands, due to repetition of the immunising epitopes.

If desired, such receptors with multiple ligands could include effector molecules or labels, so that they can be used in therapy or diagnosis as described above.

The ligand may be linked to the other part of the receptor by any suitable means, for instance by covalent or non-covalent chemical linkages. However, where the receptor comprises a ligand and another protein molecule, it is preferred that they are produced by recombinant DNA technology as a fusion product. If necessary, a linker peptide sequence can be placed between the ligand and the other protein molecule to provide flexibility.

The basic techniques for manipulating Ig molecules by recombinant DNA technology are described in the patent references cited above. These may be adapted in order to allow for the production of ligands and receptors according to the invention by means of recombinant DNA technology.

Preferably, where the ligand is to be used for in vivo diagnosis or therapy in humans, it is humanised, for instance by CDR replacement as described in EP-A-0 239 400.

In order to obtain a DNA sequence encoding a ligand, it is generally necessary firstly to produce a hybridoma which secretes an appropriate MAb. This can be a very time consuming method. Once an immunised animal has been produced, it is necessary to fuse separated spleen cells with a suitable myeloma cell line, grow up the cell lines thus produced, select appropriate lines, reclone the selected lines and reselect. This can take some long time. This problem also applies to the production of modified Igs.

A further problem with the production of ligands, and also receptors according to the invention and modified Igs, by recombinant DNA technology is the cloning of the variable domain encoding sequences from the hybridoma which produces the MAb from which the specificity is to be derived. This can be a relatively long method involving the production of a suitable probe, construction of a clone library from cDNA or genomic DNA, extensive probing of the clone library, and manipulation of any isolated clones to enable the cloning into a suitable expression vector. Due to the inherent variability of the DNA sequences encoding Ig variable domains, it has not previously been possible to avoid such time consuming work. It is therefore a further aim of the present invention to provide a method which enables substantially any sequence encoding an Ig superfamily molecule variable domain (ligand) to be cloned in a reasonable period of time.

According to another aspect of the present invention therefore, there is provided a method of cloning a sequence (the target sequence) which encodes at least part of the variable domain of an Ig superfamily molecule, which method comprises:

(a) providing a sample of double stranded (ds) nucleic acid which contains the target sequence;
(b) denaturing the sample so as to separate the two strands;
(c) annealing to the sample a forward and a back oligonucleotide primer, the forward primer being specific for a sequence at or adjacent the 3' end of the sense strand of the target sequence, the back primer being specific for a sequence at or adjacent the 3' end of the antisense strand of the target sequence, under conditions which allow the primers to hybridise to the nucleic acid at or adjacent the target sequence;
(d) treating the annealed sample with a DNA polymerase enzyme in the presence of deoxynucleoside triphosphates under conditions which cause primer extension to take place; and
(e) denaturing the sample under conditions such that the extended primers become separated from the target sequence.

Preferably, the method of the present invention further includes the step (f) of repeating steps (c) to (e) on the denatured mixture a plurality of times.

Preferably, the method of the present invention is used to clone complete variable domains from Ig molecules, most preferably from Ig heavy chains. In the most preferred instance, the method will produce a DNA sequence encoding a ligand according to the present invention.

In step (c) recited above, the forward primer becomes annealed to the sense strand of the target sequence at or adjacent the 3' end of the strand. In a similar manner, the back primer becomes annealed to the antisense strand of the target sequence at or adjacent the 3' end of the strand. Thus, the forward primer anneals at or adjacent the region of the ds nucleic acid which encodes the C terminal end of the variable region or domain. Similarly, the back primer anneals at or adjacent the region of the ds nucleic acid which encodes the N-terminal end of the variable domain.

In step (d), nucleotides are added onto the 3' end of the forward and back primers in accordance with the sequence of the strand to which they are annealed. Primer extension will continue in this manner until stopped by the beginning of the denaturing step (e). It must therefore be ensured that step (d) is carried out for a long enough time to ensure that the primers are extended so that the extended strands totally overlap one another.

In step (e), the extended primers are separated from the ds nucleic acid. The ds nucleic acid can then serve again as a substrate to which further primers can anneal. Moreover, the extended primers themselves have the necessary complementary sequences to enable the primers to anneal thereto.

During further cycles, if step (f) is used, the amount of extended primers will increase exponentially so that at the end of the cycles there will be a large quantity of cDNA having sequences complementary to the sense and antisense strands of the target sequence. Thus, the method of the present invention will result in the accumulation of a large quantity of cDNA which can form ds cDNA encoding at least part of the variable domain.

As will be apparent to the skilled person, some of the steps in the method may be carried out simultaneously or sequentially as desired.

The forward and back primers may be provided as isolated oligonucleotides, in which case only two oligonucleotides will be used. However, alternatively the forward and back primers may each be supplied as a mixture of closely related oligonucleotides. For instance, it may be found that at a particular point in the sequence to which the primer is to anneal, there is the possibility of nucleotide variation. In this case a primer may be used for each possible nucleotide variation. Furthermore it may be possible to use two or more sets of "nested" primers in the method to enhance the specific cloning of variable region genes.

The method described above is similar to the method described by Saiki et al. [17]. A similar method is also used in the methods described in EP-A-0 200 362. In both cases the method described is carried out using primers which are known to anneal efficiently to the specified nucleotide sequence. In neither of these disclosures was it suggested that the method could be used to clone Ig parts of variable domain encoding sequences, where the target sequence contains inherently highly variable areas.

The ds nucleic acid sequence used in the method of the present invention may be derived from mRNA. For instance, RNA may be isolated in known manner from a cell or cell line which is known to produce Igs. mRNA may be separated from other RNA by oligo-dT chromatography. A complementary strand of cDNA may then be synthesised on the mRNA template, using reverse transcriptase and a suitable primer, to yield an RNA/DNA heteroduplex. A second strand of DNA can be made in one of several ways, for example, by priming with RNA fragments of the mRNA strand (made by incubating RNA/DNA heteroduplex with RNase H) and using DNA polymerase, or by priming with a synthetic oligodeoxynucleotide primer which anneals to the 3' end of the first strand and using DNA polymerase. It has been found that the method of the present invention can be carried out using ds cDNA prepared in this way.

When making such ds cDNA, it is possible to use a forward primer which anneals to a sequence in the CH1 domain (for a heavy chain variable domain) or the Cλ or Cκ domain (for a light chain variable domain). These will be located in close enough proximity to the target sequence to allow the sequence to be cloned.

The back primer may be one which anneals to a sequence at the N-terminal end of the VH1, Vκ or Vλ domain. The back primer may consist of a plurality of primers having a variety of sequences designed to be complementary to the various families of VH1, Vκ or Vλ sequences known. Alternatively the back primer may be a single primer having a consensus sequence derived from all the families of variable region genes.

Surprisingly, it has been found that the method of the present invention can be carried out using genomic DNA. If genomic DNA is used, there is a very large amount of DNA present, including actual coding sequences, introns and untranslated sequences between genes. Thus, there is considerable scope for non-specific annealing under the conditions used. However, it has surprisingly been found that there is very little non-specific annealing. It is therefore unexpected that it has proved possible to clone the genes of Ig-variable domains from genomic DNA.

Under some circumstances the use of genomic DNA may prove advantageous compared with use of mRNA, as the mRNA is readily degraded, and especially difficult to prepare from clinical samples of human tissue.

Thus, in accordance with an aspect of the present invention, the ds nucleic acid used in step (a) is genomic DNA.

When using genomic DNA as the ds nucleic acid source, it will not be possible to use as the forward primer an oligonucleotide having a sequence complementary to a sequence in a constant domain. This is because, in genomic DNA, the constant domain genes are generally separated from the variable domain genes by a considerable number of base pairs. Thus, the site of annealing would be too remote from the sequence to be cloned.

It should be noted that the method of the present invention can be used to clone both rearranged and unrearranged variable domain sequences from genomic DNA. It is known that in germ line genomic DNA the three genes, encoding the VH, DH and JH respectively, are separated from one another by considerable numbers of base pairs. On maturation of the immune response, these genes are rearranged so that the VH, DH and JH genes are fused together to provide the gene encoding the whole variable domain (see FIG. 1). By using a forward primer specific for a sequence at or adjacent the 3' end of the sense strand of the genomic "unrearranged" VH gene, it is possible to clone the "unrearranged" VH gene alone, without also cloning the DH and JH genes. This can be of use in that it will then be possible to fuse the VH gene onto pre-cloned or synthetic DH and DH genes. In this way, rearrangement of the variable domain genes can be carried out in vitro.

The oligonucleotide primers used in step (c) may be specifically designed for use with a particular target sequence. In this case, it will be necessary to sequence at least the 5' and 3' ends of the target sequence so that the appropriate oligonucleotides can be synthesised. However, the present inventors have discovered that it is not necessary to use such specifically designed primers. Instead, it is possible to use a species specific general primer or a mixture of such primers for annealing to each end of the target sequence. This is not particularly surprising as regards the 3' end of the target sequence. It is known that this end of the variable domain encoding sequence leads into a segment encoding JH which is known to be relatively conserved. However, it was surprisingly discovered that, within a single species, the sequence at the 5' end of the target sequence is sufficiently well conserved to enable a species specific general primer or a mixture thereof to be designed for the 5' end of the target sequence.

Therefore according to a preferred aspect of the present invention, in step (c) the two primers which are used are species specific general primers, whether used as single primers or as mixtures of primers. This greatly facilitates the cloning of any undetermined target sequence since it will avoid the need to carry out any sequencing on the target sequence in order to produce target sequence-specific primers. Thus the method of this aspect of the invention provides a general method for cloning variable region or domain encoding sequences of a particular species.

Once the variable domain gene has been cloned using the method described above, it may be directly inserted into an expression vector, for instance using the PCR reaction to paste the gene into a vector.

Advantageously, however, each primer includes a sequence including a restriction enzyme recognition site. The sequence recognised by the restriction enzyme need not be in the part of the primer which anneals to the ds nucleic acid, but may be provided as an extension which does not anneal. The use of primers with restriction sites has the advantage that the DNA can be cut with at least one restriction enzyme which leaves 3' or 5' overhanging nucleotides. Such DNA is more readily cloned into the corresponding sites on the vectors than blunt end fragments taken directly from the method. The ds cDNA produced at the end of the cycles will thus be readily insertable into a cloning vector by use of the appropriate restriction enzymes. Preferably the choice of restriction sites is such that the ds cDNA is cloned directly into an expression vector, such that the ligand encoded by the gene is expressed. In this case the restriction site is preferably located in the sequence which is annealed to the ds nucleic acid.

Since the primers may not have a sequence exactly complementary to the target sequence to which it is to be annealed, for instance because of nucleotide variations or because of the introduction of a restriction enzyme recognition site, it may be necessary to adjust the conditions in the annealing mixture to enable the primers to anneal to the ds nucleic acid. This is well within the competence of the person skilled in the art and needs no further explanation.

In step (d), any DNA polymerase may be used. Such polymerases are known in the art and are available commercially. The conditions to be used with each polymerase are well known and require no further explanation here. The polymerase reaction will need to be carried out in the presence of the four nucleoside triphosphates. These and the polymerase enzyme may already be present in the sample or may be provided afresh for each cycle.

The denaturing step (e) may be carried out, for instance, by heating the sample, by use of chaotropic agents, such as urea or guanidine, or by the use of changes in ionic strength or pH. Preferably, denaturing is carried out by heating since this is readily reversible. Where heating is used to carry out the denaturing, it will be usual to use a thermostable DNA polymerase, such as Taq polymerase, since this will not need replenishing at each cycle.

If heating is used to control the method, a suitable cycle of heating comprises denaturation at about 95° C. for about 1 minute, annealing at from 30° C. to 65° C. for about 1 minute and primer extension at about 75° C. for about 2 minutes. To ensure that elongation and renaturation is completer the mixture after the final cycle is preferably held at about 60° C. for about 5 minutes.

The product ds cDNA may be separated from the mixture for instance by gel electrophoresis using agarose gels. However, if desired, the ds cDNA may be used in unpurified form and inserted directly into a suitable cloning or expression vector by conventional methods. This will be particularly easy to accomplish if the primers include restriction enzyme recognition sequences.

The method of the present invention may be used to make variations in the sequences encoding the variable domains. For example this may be achieved by using a mixture of related oligonucleotide primers as at least one of the primers. Preferably the primers are particularly variable in the middle of the primer and relatively conserved at the 5' and 3' ends. Preferably the ends of the primers are complementary to the framework regions of the variable domain, and the variable region in the middle of the primer covers all or part of a CDR. Preferably a forward primer is used in the area which forms the third CDR. If the method is carried out using such a mixture of oligonucleotides, the product will be a mixture of variable domain encoding sequences. Moreover, variations in the sequence may be introduced by incorporating some mutagenic nucleotide triphosphates in step (d), such that point mutations are scattered throughout the target region. Alternatively such point mutations are introduced by performing a large number of cycles of amplification, as errors due to the natural error rate of the DNA polymerase are amplified, particularly when using high concentrations of nucleoside triphosphates.

The method of this aspect of the present invention has the advantage that it greatly facilitates the cloning of variable domain encoding sequences directly from mRNA or genomic DNA. This in turn will facilitate the production of modified Ig-type molecules by any of the prior art methodes referred to above. Further, target genes can be cloned from tissue samples containing antibody producing cells, and the genes can be sequenced. By doing this, it will be possible to look directly at the immune repertoire of a patient. This "fingerprinting" of a patient's immune repertoire could be of use in diagnosis, for instance of auto-immune diseases.

In the method for amplifying the amount of a gene encoding a variable domain, a single set of primers is used in several cycles of copying via the polymerase chain reaction. As a less preferred alternative, there is provided a second method which comprises steps (a) to (d) as above, which further includes the steps of:

(g) treating the sample of ds cDNA with traces of DNAse in the presence of DNA polymerase I to allow nick translation of the DNA; and (h) cloning the ds cDNA into a vector.

If desired, the second method may further include the steps of:

(i) digesting the DNA of recombinant plasmids to release DNA fragments containing genes encoding variable domains; and (j) treating the fragments in a further set of steps (c) to (h).

Preferably the fragments are separated from the vector and from other fragments of the incorrect size by gel electrophoresis.

The steps (a) to (d) then (g) to (h) can be followed once, but preferably the entire cycle (c) to (d) and (g) to (j) is repeated at least once. In this way a priming step in which the genes are specifically copied, is followed by a cloning step, in which the amount of genes is increased.

In step (a) the ds cDNA is derived from mRNA. For Ig derived variable domains, the mRNA is preferably be isolated from lymphocytes which have been stimulated to enhance production of mRNA.

In each step (c) the set of primers are preferably different from the previous step (c), so as to enhance the specificity of copying. Thus the sets of primers form a nested set. For example, for cloning of Ig heavy chain variable domains, the first set of primers may be located within the signal sequence and constant region, as described by Larrick et al., [18], and the second set of primers entirely within the variable region, as described by Orlandi et al., [19]. Preferably the primers of step (c) include restriction sites to facilitate subsequent cloning. In the last cycle the set of primers used in step (c) should preferably include restriction sites for introduction into expression vectors. In step (g) possible mismatches between the primers and the template strands are corrected by "nick translation". In step (h), the ds cDNA is preferably cleaved with restriction enzymes at sites introduced into the primers to facilitate the cloning.

According to another aspect of the present invention the product ds cDNA is cloned directly into an expression vector. The host may be prokaryotic or eukaryotic, but is preferably bacterial. Preferably the choice of restriction sites in the primers and in the vector, and other features of the vector will allow the expression of complete ligands, while preserving all those features of the amino acid sequence which are typical of the (methoded) ligands. For example, for expression of the rearranged variable genes, the primers would be chosen to allow the cloning of target sequences including at least all the three CDR sequences. The cloning vector would then encode a signal sequence (for secretion of the ligand), and sequences encoding the N-terminal end of the first framework region, restriction sites for cloning and then the C-terminal end of the last (fourth) framework region.

For expression of unrearranged VH genes as part of complete ligands, the primers would be chosen to allow the cloning of target sequences including at least the first two CDRs. The cloning vector could then encode signal sequence, the N-terminal end of the first framework region, restriction sites for cloning and then the C-terminal end of the third framework region, the third CDR and fourth framework region.

Primers and cloning vectors may likewise be devised for expression of single CDRs, particularly the third CDR, as parts of complete ligands. The advantage of cloning repertoires of single CDRs would permit the design of a "universal" set of framework regions, incorporating desirable properties such as solubility.

Single ligands could be expressed alone or in combination with a complementary variable domain. For example, a heavy chain variable domain can be expressed either as an individual domain or, if it is expressed with a complementary light chain variable domain, as an antigen binding site. Preferably the two partners would be expressed in the same cell, or secreted from the same cell, and the proteins allowed to associate non-covalently to form an Fv fragment. Thus the two genes encoding the complementary partners can be placed in tandem and expressed from a single vector, the vector including two sets of restriction sites.

Preferably the genes are introduced sequentially: for example the heavy-chain variable domain can be cloned first and then the light chain variable domain. Alternatively the two genes are introduced into the vector in a single step, for example by using the polymerase chain reaction to paste together each gene with any necessary intervening sequence, as essentially described by Yon and Fried [29]. The two partners could be also expressed as a linked protein to produce a single chain Fv fragment, using similar vectors to those described above. As a further alternative the two genes may be placed in two different vectors, for example in which one vector is a phage vector and the other is a plasmid vector.

Moreover, the cloned ds cDNA may be inserted into an expression vector already containing sequences encoding one or more constant domains to allow the vector to express Ig-type chains. The expression of Fab fragments, for example, would have the advantage over Fv fragments that the heavy and light chains would tend to associate through the constant domains in addition to the variable domains. The final expression product may be any of the modified Ig-type molecules referred to above.

The cloned sequence may also be inserted into an expression vector so that it can be expressed as a fusion protein. The variable domain encoding sequence may be linked directly or via a linker sequence to a DNA sequence encoding any protein effector molecule, such as a toxin, enzyme, label or another ligand. The variable domain sequences may also be linked to proteins on the outer side of bacteria or phage. Thus, the method of this aspect of the invention may be used to produce receptors according to the invention.

According to another aspect of the invention, the cloning of ds cDNA directly for expression permits the rapid construction of expression libraries which can be screened for binding activities. For Ig heavy and light chain variable genes, the ds cDNA may comprise variable genes isolated as complete rearranged genes from the animal, or variable genes built from several different sources, for example a repertoire of unrearranged VH genes combined with a synthetic repertoire of DH and JH genes. Preferably repertoires of genes encoding Ig heavy chain variable domains are prepared from lymphocytes of animals immunised with an antigen.

The screening method may take a range of formats well known in the art. For example Ig heavy chain variable domains secreted from bacteria may be screened by binding to antigen on a solid phase, and detecting the captured domains by antibodies. Thus the domains may be screened by growing the bacteria in liquid culture and binding to antigen coated on the surface of ELISA plates. However, preferably bacterial colonies (or phage plaques) which secrete ligands (or modified ligands, or ligand fusions with proteins) are screened for antigen binding on membranes. Either the ligands are bound directly to the membranes (and for example detected with labelled antigen), or captured on antigen coated membranes (and detected with reagents specific for ligands). The use of membranes offers great convenience in screening many clones, and such techniques are well known in the art.

The screening method may also be greatly facilitated by making protein fusions with the ligands, for example by introducing a peptide tag which is recognised by an antibody at the N-terminal or C-terminal end of the ligand, or joining the ligand to an enzyme which catalyses the conversion of a colourless substrate to a coloured product. In the latter case, the binding of antigen may be detected simply by adding substrate. Alternatively, for ligands expressed and folded correctly inside eukaryotic cells, joining of the ligand and a domain of a transcriptional activator such as the GAL4 protein of yeast, and joining of antigen to the other domain of the GAL4 protein, could form the basis for screening binding activities, as described by Fields and Song [21].

The preparation of proteins, or even cells with multiple copies of the ligands, may improve the avidity of the ligand for immobilised antigen, and hence the sensitivity of the screening method. For example, the ligand may be joined to a protein subunit of a multimeric protein, to a phage coat protein or to an outer membrane protein of *E. coli* such as ompA or lamB. Such fusions to phage or bacterial proteins also offers possibilities of selecting bacteria displaying ligands with antigen binding activities. For example such bacteria may be precipitated with antigen bound to a solid support, or may be subjected to affinity chromatography, or may be bound to larger cells or particles which have been coated with antigen and sorted using a fluorescence activated cell sorter (FACS). The proteins or peptides fused to the ligands are preferably encoded by the vector, such that cloning of the ds cDNA repertoire creates the fusion product.

In addition to screening for binding activities of single ligands, it may be necessary to screen for binding or catalytic activities of associated ligands, for example, the associated Ig heavy and light chain variable domains. For example, repertoires of heavy and light chain variable genes may be cloned such that two domains are expressed together. Only some of the pairs of domains may associate, and only some of these associated pairs may bind to antigen. The repertoires of heavy and light chain variable domains could be cloned such that each domain is paired at random. This approach may be most suitable for isolation of associated domains in which the presence of both partners is required to form a cleft. Alternatively, to allow the binding of hapten. Alternatively, since the repertoires of light chain sequences are less diverse than those of heavy chains, a small repertoire of light chain variable domains, for example including representative members of each family of domains, may be combined with a large repertoire of heavy chain variable domains.

Preferably however, a repertoire of heavy chain variable domains is screened first for antigen binding in the absence of the light chain partner, and then only those heavy chain variable domains binding to antigen are combined with the repertoire of light chain variable domains. Binding of associated heavy and light chain variable domains may be distinguished readily from binding of single domains, for example by fusing each domain to a different C-terminal peptide tag which are specifically recognised by different monoclonal antibodies.

The hierarchical approach of first cloning heavy chain variable domains with binding activities, then cloning matching light chain variable domains may be particularly appropriate for the construction of catalytic antibodies, as the heavy chain may be screened first for substrate binding. A light chain variable domain would then be identified which is capable of association with the heavy chain, and "catalytic" residues such as cysteine or histidine (or prosthetic groups) would be introduced into the CDRs to stabilise the transition state or attack the substrate, as described by Baldwin and Schultz [22].

Although the binding activities of non-covalently associated heavy and light chain variable domains (Fv fragments) may be screened, suitable fusion proteins may drive the association of the variable domain partners. Thus Fab fragments are more likely to be associated than the Fv fragments, as the heavy chain variable domain is attached to a single heavy chain constant domain, and the light chain variable domain is attached to a single light chain variable domain, and the two constant domains associate together.

Alternatively the heavy and light chain variable domains are covalently linked together with a peptide, as in the single chain antibodies, or peptide sequences attached, preferably at the C-terminal end which will associate through forming cysteine bonds or through non-covalent interactions, such as the introduction of "leucine zipper" motifs. However, in order to isolate pairs of tightly associated variable domains, the Fv fragments are preferably used.

The construction of Fv fragments isolated from a repertoire of variable region genes offers a way of building complete antibodies, and an alternative to hybridoma technology. For example by attaching the variable domains to light or suitable heavy chain constant domains, as appropriate, and expressing the assembled genes in mammalian cells, complete antibodies may be made and should possess natural effector functions, such as complement lysis. This route is particularly attractive for the construction of human monoclonal antibodies, as hybridoma technology has proved difficult, and for example, although human peripheral blood lymphocytes can be immortalised with Epstein Barr virus, such hybridomas tend to secrete low affinity IgM antibodies.

Moreover, it is known that immmunological mechanisms ensure that lymphocytes do not generally secrete antibodies directed against host proteins. However it is desirable to make human antibodies directed against human proteins, for example to human cell surface markers to treat cancers, or to histocompatibility antigens to treat auto-immune diseases. The construction of human antibodies built from the combinatorial repertoire of heavy and light chain variable domains may overcome this problem, as it will allow human antibodies to be built with specificities which would normally have been eliminated.

The method also offers a new way of making bispecific antibodies. Antibodies with dual specificity can be made by fusing two hybridomas of different specificities, so as to make a hybrid antibody with an Fab arm of one specificity, and the other Fab arm of a second specificity. However the yields of the bispecific antibody are low, as heavy and light chains also find the wrong partners. The construction of Fv fragments which are tightly associated should preferentially drive the association of the correct pairs of heavy with light chains. (It would not assist in the correct pairing of the two heavy chains with each other.) The improved production of bispecific antibodies would have a variety of applications in diagnosis and therapy, as is well known.

Thus the invention provides a species specific general oligonucleotide primer or a mixture of such primers useful for cloning variable domain encoding sequences from animals of that species. The method allows a single pair or pair of mixtures of species specific general primers to be used to clone any desired antibody specificity from that species. This eliminates the need to carry out any sequencing of the target sequence to be cloned and the need to design specific primers for each specificity to be recovered.

Furthermore it provides for the construction of repertoires of variable genes, for the expression of the variable genes directly on cloning, for the screening of the encoded domains for binding activities and for the assembly of the domains with other variable domains derived from the repertoire.

Thus the use of the method of the present invention will allow for the production of heavy chain variable domains with binding activities and variants of these domains. It allows for the production of monoclonal antibodies and bispecific antibodies, and will provide an alternative to hybridoma technology. For instance, mouse splenic ds mRNA or genomic DNA may be obtained from a hyperimmunised mouse. This could be cloned using the method of the present invention and then the cloned ds DNA inserted into a suitable expression vector. The expression vector would be used to transform a host cell, for instance a bacterial cell, to enable it to produce an Fv fragment or a Fab fragment. The Fv or Fab fragment would then be built into a monoclonal antibody by attaching constant domains and expressing it in mammalian cells.

The present invention is now described, by way of example only, with reference to the accompanying drawings in which:

FIG. 1 shows a schematic representation of the unrearranged and rearranged heavy and light chain variable genes and the location of the primers;

FIG. 3 shows the sequence of the Ig variable region derived sequences in M13-VHPCR1;

FIG. 5 shows the sequence of the Ig variable region derived sequences in M13-VKPCR1;

FIG. 6 shows the nucleotide sequences of the heavy and light chain variable domain encoding sequences of MAb MBr1;

Figure 16:
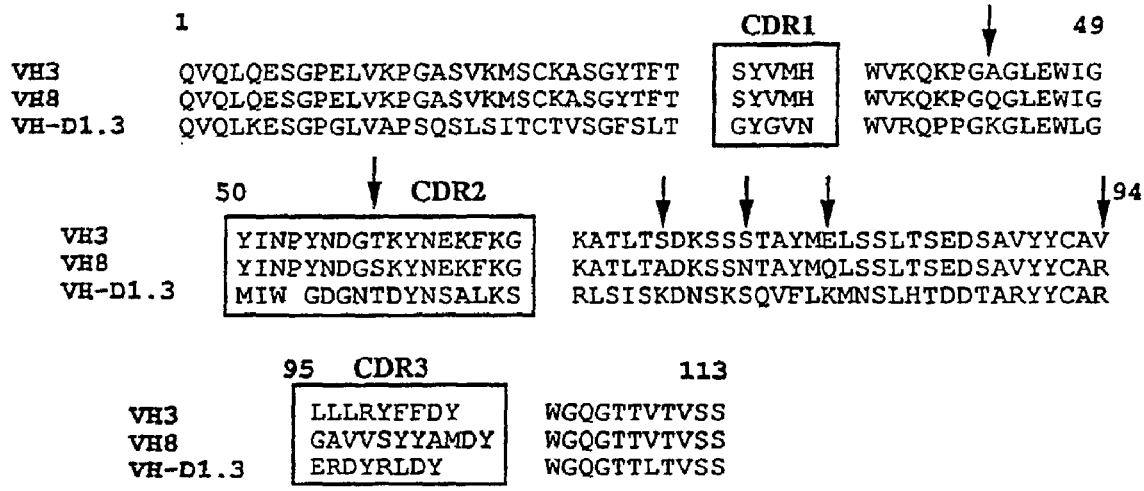
Figure 17:
Figure 18:
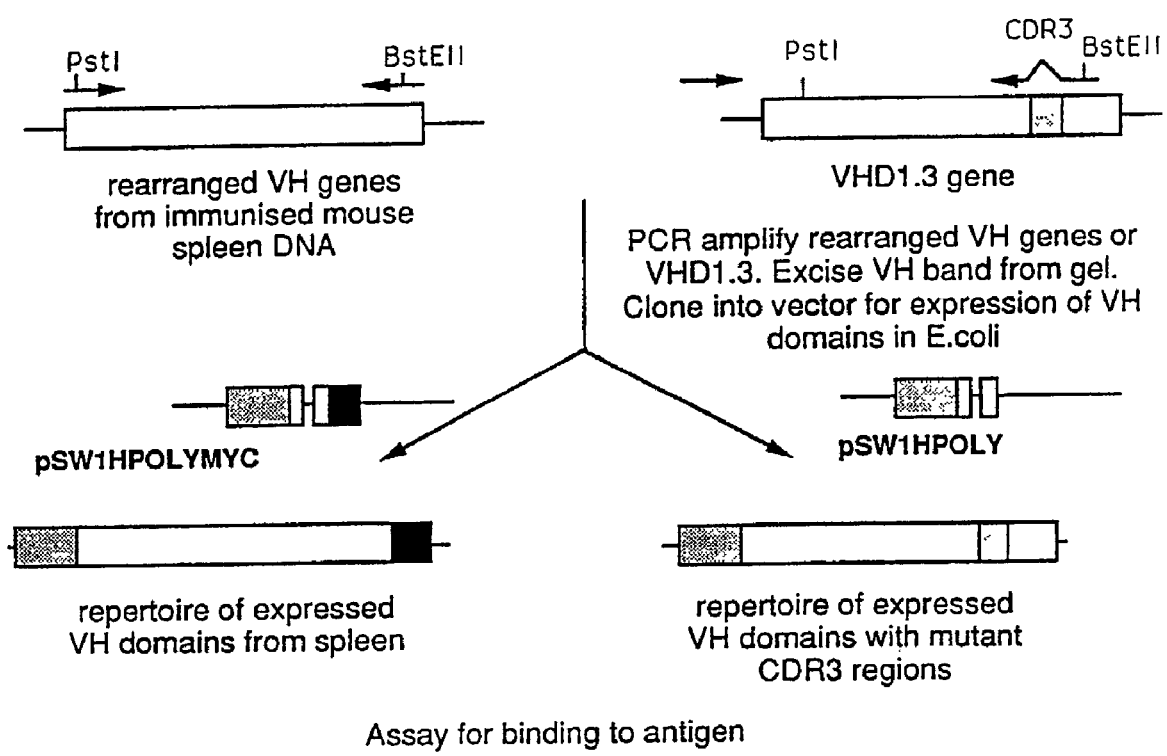

FIG. 8 shows a schematic representation of the pSV-hygro vector (also known as α-Lys 17). It is derived from pSV gpt vector with the gene encoding mycophenolic acid replaced by a gene coding for hygromycin resistance. The construct contains a variable gene cloned as a HindIII-BamHI fragment which is excised on introducing the new variable region. The gene for human Cκ has also been engineered to remove a BamHI site, such that the BamHI site in the vector is unique;

FIG. 9 shows the assembly of the mouse: human MBr1 chimaeric antibody;

FIG. 10 shows encoded amino acid sequences of 48 mouse rearranged VH genes;

FIG. 11 shows encoded amino acid sequences of human rearranged VH genes;

FIG. 12 shows encoded amino acid sequences of unrearranged human VH genes;

FIG. 13 shows the sequence of part of the plasmid pSW1: essentially the sequence of a pectate lyase leader linked to VHLYS in pSW1 and cloned as an SphI-EcoRI fragment into pUC19 and the translation of the open reading frame encoding the pectate lyase leader-VHLYS polypeptide being shown;

FIG. 14 shows the sequence of part of the plasmid pSW2: essentially the sequence of a pectate lyase leader linked to VHLYS and to VKLYS, and cloned as an SphI-EcoRI-EcoRI fragment into pUC19 and the translation of open reading frames encoding the pectate lyase leader-VHLYS and pectate lyase leader-VKLYS polypeptides being shown;

FIG. 15 shows the sequence of part of the plasmid pSW1HPOLYMYC which is based on pSW1 and in which a polylinker sequence has replaced the variable domain of VHLYS, and acts as a cloning site for amplified VH genes, and a peptide tag is introduced at the C-terminal end;

FIG. 16 shows the encoded amino acid sequences of two VH domains derived from mouse spleen and having lysozyme binding activity, and compared with the VH domain of the D1,3 antibody. The arrows mark the points of difference between the two VH domains;

FIG. 17 shows the encoded amino acid sequence of a VH domain derived from human peripheral blood lymphocytes and having lysozyme binding activity;

FIG. 18 shows a scheme for generating and cloning mutants of the VHLYS gene, which is compared with the scheme for cloning natural repertoires of VH genes;

FIG. 19 shows the sequence of part of the vector pSW2HPOLY;

FIG. 20 shows the sequence of part of the vector pSW3 which encodes the two linked VHLYS domains;

FIG. 21 shows the sequence of the VHLYS domain and pelB leader sequence fused to the alkaline phosphatase gene;

FIG. 22 shows the sequence of the vector pSW1VHLYS-VKPOLYMYC for expression of a repertoire of Vκ light chain variable domains in association with the VHLYS domain; and FIG. 23 shows the sequence of VH domain which is secreted at high levels from *E. coli*. The differences with VHLYS domain are marked.

PRIMERS

In the Examples described below, the following oligonucleotide primers, or mixed primers were used. Their locations are marked on FIG. 1 and sequences are as follows:

```
VH1FOR      5' TGAGGAGACGGTGACCGTGGTCCCTTGGCCCCAG 3';
VH1FOR-2    5' TGAGGAGACGGTGACCGTGGTCCCTTGGCCCC 3';

Hu1VHFOR    5' CTTGGTGGAGGCTGAGGAGACGGTGACC 3';
Hu2VHFOR    5' CTTGGTGGAGGCTGAGGAGACGGTGACC 3';
Hu3VHFOR    5' CTTGGTGGATGCTGAGGAGACGGTGACC 3';
Hu4VHFOR    5' CTTGGTGGATGCTGATGAGACGGTGACC 3';

MOJH1FOR    5' TGAGGAGACGGTGACCGTGGTCCCTGCGCCCCAG 3';
MOJE2FOR    5' TGAGGAGACGGTGACCGTGGTGCCTTGGCCCCAG 3';
MOJH3FOR    5' TGCAGAGACGGTGACCAGAGTCCCTTGGCCCCAG 3';
MOJH4FOR    5' TGAGGAGACGGTCACCGAGGTTCCTTGACCCCAG 3';

HUJH1FOR    5' TGAGGAGACGGTGACCAGGGTGCCCTGGCCCCAG 3';
HUJH2FOR    5' TGAGGAGACGGTGACCAGGGTGCCACGGCCCCAG 3';
HUJH4FOR    5' TGAGGAGACGGTGACCAGGGTTCCTTGGCCCCAG 3';

VK1FOR      5' GTTAGATCTCCAGCTTGGTCCC 3';
VX2FOR      5' CGTTAGATCTCCAGCTTGGTCCC 3';
VK3FOR      5' CCGTTTCAGCTCGAGCTTGGTCCC 3';
```

```
                   -continued
MOJK1FOR    5' CGTTAGATCTCCAGCTTGGTGCC 3';
MOJK3FOR    5' GGTTAGATCTCCAGTCTGGTCCC 3';
MOJK4FOR    5' CGTTAGATCTCCAACTTTGTCCC 3';

HUJK1FOR    5' CGTTAGATCTCCACCTTGGTCCC 3';
HUJK3FOR    5' CGTTAGATCTCCACTTTGGTCCC 3';
HUJK4FOR    5' CGTTAGATCTCCACCTTGGTCCC 3';
HUJK5FOR    5' CGTTAGATCTCCAGTCGTGTCCC 3';

VH1BACK       5' AGGT(C/G)(C/A)A(G/A)CTGCAG(G/C)AGTC(T/A)GG 3';
Hu2VHIBACK:   5' CAGGTGCAGCTGCAGCAGTCTGG 3';
HuVHIIBACK:   5' CAGGTGCAGCTGCACGAGTCGGG 3';
Hu2VHIIIBACK: 5' GAGGTGCAGCTGCAGGAGTCTGG 3';
HuVHIVBACK:   5' CAGGTGCAGCTGCAGCAGTCTGG 3';

MOVHIBACK     5' AGGTGCAGCTGCAGGAGTCAG 3';
MOVHIIABACK   5' AGGTCCAGCTGCAGCA(G/A)TCTGG 3';
MOVHIIBBACK   5' AGGTCCAACTGCAGCAGCCTGG 3';
MOVHIIBACK    5' AGGTGAAGCTGCAGGAGTCTGG 3';

VK1BACK     5' GACATTCAGCTGACCCAGTCTCCA 3';
VK2BACK     5' GACATTGAGCTCACCCAGTCTCCA 3';

MOVKIIABACK  5' GATGTTCAGCTGACCCAAACTCCA 3'
MOVKIIBBACK  5' GATATTCAGCTGACCCAGGATGAA 3';

HuHep1FOR    5' C(A/G)(C/G) TGAGCTCACTGTGTCTCTCGCACA 3';
HuOcta1BACK  5' CGTGAATATGCAAATAA 3';
HuOcta2BACK  5' AGTAGGAGACATGCAAAT 3'; and
HuOcta3BACK  5' CACCACCCACATGCAAAT 3';

VHMUT1      5' GGAGACGGTGACCGTGGTCCCTTGGCCCCAGTAGTCAAG
               NNNNNNNNNNNNNCTCTCTGGC 3' (where N is an
               equimolar mixture of T, C, G and A)

M13 pRIMER  5' AACAGCTATGACCATG 3' (New England Biolabs
               *1201)
```

EXAMPLE 1

Cloning of Mouse Rearranged Variable Region Genes from Hybridomas, Assembly of Genes Encoding Chimaeric Antibodies and the Expression of Antibodies from Myeloma Cells VH1FOR is designed to anneal with the 3' end of the sense strand of any mouse heavy chain variable domain encoding sequence. It contains a BstEII recognition site. VK1FOR is designed to anneal with the 3' end of the sense strand of any mouse kappa-type light chain variable domain encoding sequence and contains a BglII recognition site. VH1BACK is designed to anneal with the 3' end of the antisense strand of any mouse heavy chain variable domain and contains a PstI recognition site. VK1BACK is designed to anneal with the 3' end of the antisense strand of any mouse kappa-type light chain variable domain encoding sequence and contains a PvuII recognition site.

In this Example five mouse hybridomas were used as a source of ds nucleic acid. The hybridomas produce monoclonal antibodies (MAbs) designated MBr1 [23], BW431/26 [24], BW494/32 [25], BW250/183 [24,26] and BW704/152 [27]. MAb MBr1 is particularly interesting in that it is known to be specific for a saccharide epitope on a human mammary carcinoma line MCF-7 [28].

Cloning Via mRNA

Each of the five hybridomas referred to above was grown up in roller bottles and about 5×10⁸ cells of each hybridoma were used to isolate RNA. mRNA was separated from the isolated RNA using oligodT cellulose [29]. First strand cDNA was synthesised according to the procedure described by Maniatis et al. [30] as set out below.

In order to clone the heavy chain variable domain encoding sequence, a 50 µl reaction solution which contains 10 µg mRNA, 20 pmole VH1FOR primer, 250 µM each of dATP, dTTP, dCTP and dGTP, 10 mM dithiothreitol (DTT), 100 mM Tris.HCl, 10 mM MgCl$_2$ and 140 mM KCl, adjusted to pH 8.3 was prepared. The reaction solution was heated at 70° C. for ten minutes and allowed to cool to anneal the primer to the 3' end of the variable domain encoding sequence in the mRNA. To the reaction solution was then added 46 units of reverse transcriptase (Anglian Biotec) and the solution was then incubated at 42° C. for 1 hour to cause first strand cDNA synthesis.

In order to clone the light chain variable domain encoding sequence, the same procedure as set out above was used except that the VK1FOR primer was used in place of the VH1FOR primer.

Amplification from RNA/DNA Hybrid

Once the ds RNA/DNA hybrids had been produced, the variable domain encoding sequences were amplified as follows. For heavy chain variable domain encoding sequence amplification, a 50 µl reaction solution containing 5 µl of the ds RNA/DNA hybrid-containing solution, 25 pmole each of VH1FOR and VH1BACK primers, 250 µM of dATP, dTTP, dCTP and dGTP, 67 mM Tris.HCl, 17 mM ammonium sulphate, 10 mM MgCl$_2$, 200 µg/ml gelatine and 2 units Taq polymerase (Cetus) was prepared. The reaction solution was overlaid with paraffin oil and subjected to 25 rounds of temperature cycling using a Techne PHC-1 programmable heating block. Each cycle consisted of 1 minute and 95° C. (to denature the nucleic acids), 1 minute at 30° C. (to anneal the primers to the nucleic acids) and 2 minutes at 72° C. (to cause elongation from the primers). After the 25 cycles, the reaction solution and the oil were extracted twice with ether, once with phenol and once with phenol/CHCl3. Thereafter ds cDNA was precipitated with ethanol. The precipitated ds cDNA was then taken up in 50 µl of water and frozen.

The procedure for light chain amplification was exactly as described above, except that the VK1FOR and VK1BACK primers were used in place of the VH1FOR and VH1BACK primers respectively.

5 µl of each sample of amplified cDNA was fractionated on 2% agarose gels by electrophoresis and stained with ethidium bromide. This showed that the amplified ds cDNA gave a major band of the expected size (about 330 bp). (However the band for VK DNA of MBr1 was very weak. It was therefore excised from the gel and reamplified in a second round.) Thus by this simple procedure, reasonable quantities of ds DNA encoding the light and heavy chain variable domains of the five MAbs were produced.

Heavy Chain Vector Construction

Figure 2:
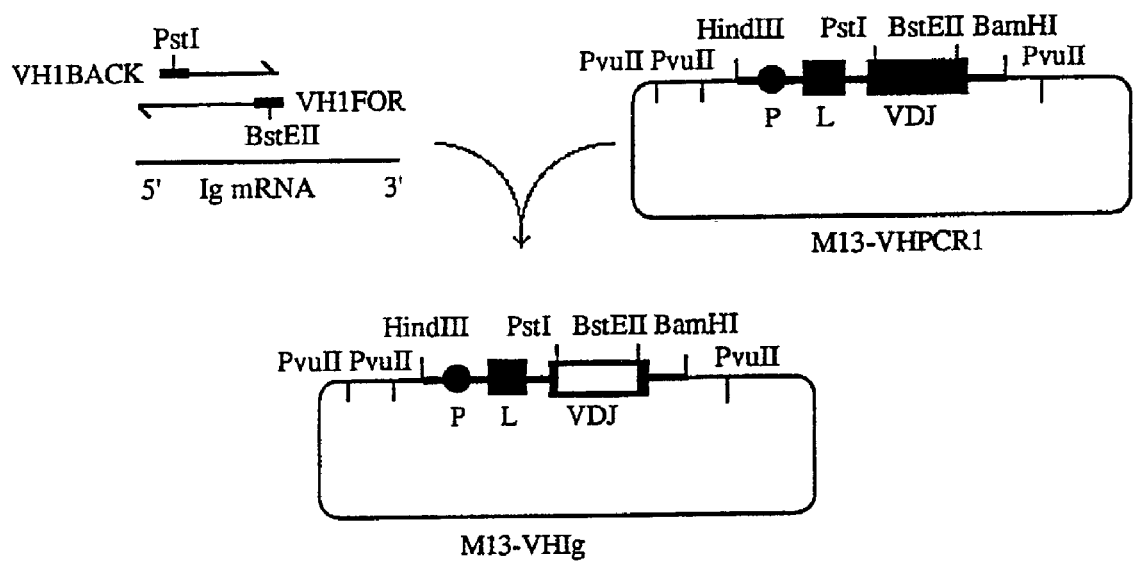
FIG. 2 shows a schematic representation of the M13-VHPCR1 vector and a cloning scheme for amplified heavy chain variable domains.

A BstEII recognition site was introduced into the vector M13-HuVHNP [31] by site directed mutagenesis [32,33] to produce the vector M13-VHPCR1 (FIGS. 2 and 3).

Each amplified heavy chain variable domain encoding sequence was digested with the restriction enzymes PstI and BstEII. The fragments were phenol extracted, purified on 2% low melting point agarose gels and force cloned into vector M13-VHPCR1 which had been digested with PstI and BstEII and purified on an 0.8% agarose gel. Clones containing the variable domain inserts were identified directly by sequencing [34] using primers based in the 3' non-coding variable gene in the M13-VHPCR1 vector.

There is an internal PstI site in the heavy chain variable domain encoding sequences of BW431/26. This variable domain encoding sequence was therefore assembled in two steps. The 3' PstI-BstEII fragment was first cloned into M13-VHPCR1, followed in a second step by the 5' PstI fragment.

Light Chain Vector Construction

Figure 4:
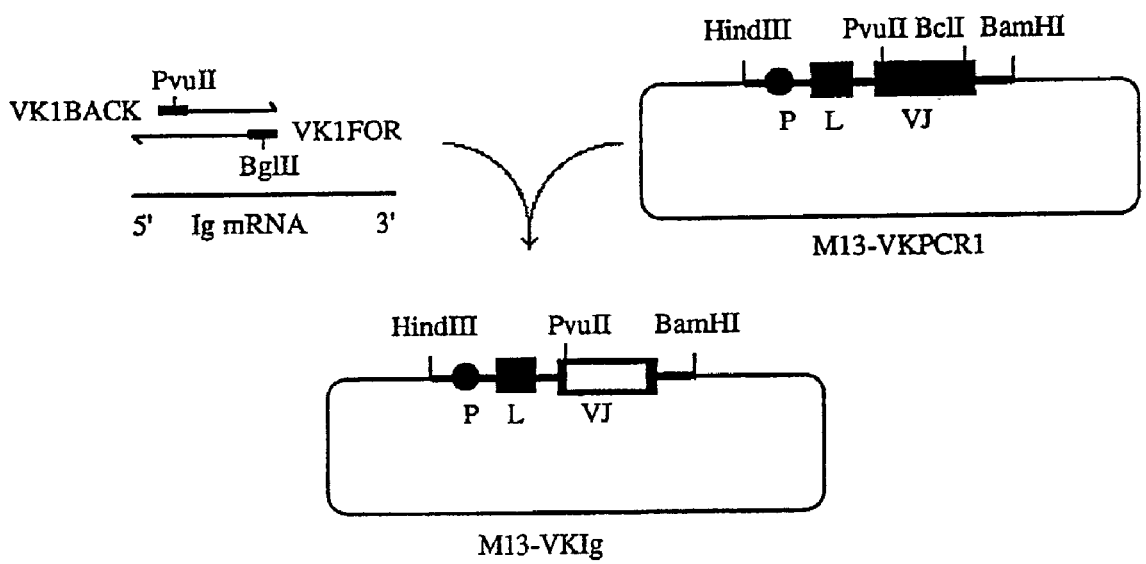
FIG. 4 shows a schematic representation of the M13-VKPCR1 vector and a cloning scheme for light chain variable domains.

Vector M13 mp18 [35] was cut with PvuII and the vector backbone was blunt ligated to a synthetic HindIII-BamHI polylinker. Vector M13-HuVKLYS [36] was digested with HindIII and BamHI to isolate the HuVKLYS gene. This HindIII-BamHI fragment was then inserted into the HindIII-BamHI polylinker site to form a vector M13-VKPCR1 which lacks any PvuII sites in the vector backbone (FIGS. 4 and 5). This vector was prepared in E Coli JM110 [22] to avoid dam methylation at the BclI site.

Each amplified light chain variable domain encoding sequence was digested with PvuII and BglII. The fragments were phenol extracted, purified on 2% low melting point agarose gels and force cloned into vector M13-VKPCR1 which had been digested with PvuII and BclI, purified on an 0.8% agarose gel and treated with calf intestinal phosphatase. Clones containing the light chain variable region inserts were identified directly by sequencing [34] using primers based in the 3' non-coding region of the variable domain in the M13-VKPCR1 vector.

The nucleotide sequences of the MBr1 heavy and light chain variable domains are shown in FIG. 6 with part of the flanking regions of the M13-VHPCR1 and M13-VKPCR1 vectors.

Antibody Expression

Figure 7:
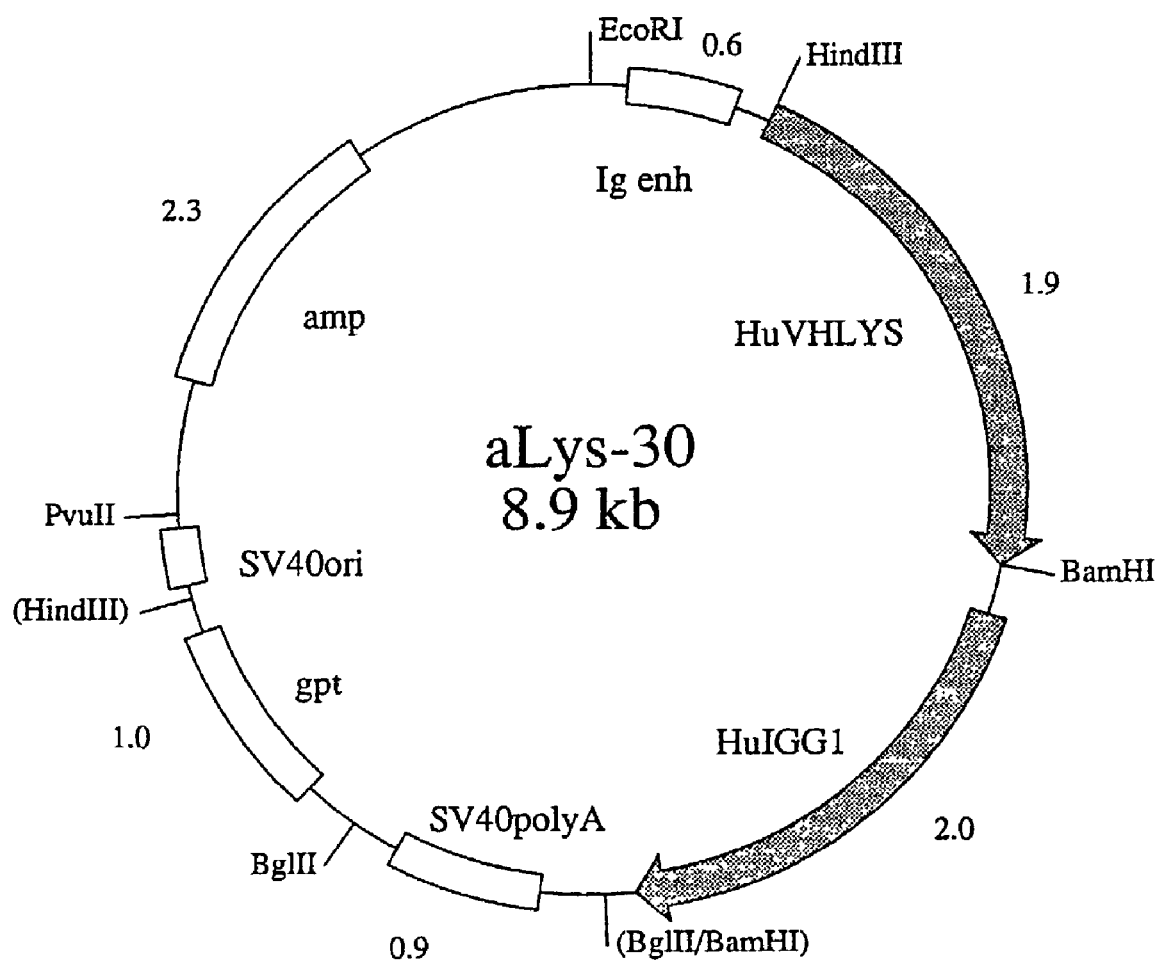
FIG. 7 shows a schematic representation of the pSV-gpt vector (also known as α-Lys 30) which contains a variable region cloned as a HindIII-BamHI fragment, which is excised on introducing the new variable region. The gene for human IgG1 has also been engineered to remove a BamHI site, such that the BamHI site in the vector is unique.

The HindIII-BamHI fragment carrying the MBr1 heavy chain variable domain encoding sequence in M13-VHPCR1 was recloned into a pSV-gpt vector with human γ1 constant regions [37] (FIG. 7). The MBr1 light chain variable domain encoding sequence in M13-VKPCR1 was recloned as a HindIII-BamHI fragment into a pSV vector, PSV-hyg-HuCK with a hygromycin resistance marker and a human kappa constant domain (FIG. 8). The assembly of the genes is summarised in FIG. 9.

The vectors thus produced were linearised with PvuI (in the case of the pSV-hygro vectors the PvuI digest is only partial) and cotransfected into the non-secreting mouse myeloma line NSO [38] by electroporation [39]. One day after cotransfection, cells were selected in 0.3 µg/ml mycophenolic acid (MPA) and after seven days in 1 µg/ml MPA. After 14 days, four wells, each containing one or two major colonies, were screened by incorporation of $^{14}C$-lysine [40] and the secreted antibody detected after precipitation with protein-A Sepharose™ (Pharmacia) on SDS-PAGE [41]. The gels were stained, fixed, soaked in a fluorographic reagent, Amplify™ (Amersham), dried and autoradiographed on preflashed film at −70° C. for 2 days.

Supernatant was also tested for binding to the mammary carcinoma line MCF-7 and the colon carcinoma line HT-29, essentially as described by Menard et al. [23], either by an indirect immunoflorescence assay on cell suspensions (using a fluorescein-labelled goat anti-human IgG (Amersham)) or by a solid phase RIA on monolayers of fixed cells (using $^{125}I$-protein A (Amersham)).

It was found that one of the supernatants from the four wells contained secreted antibody. The chimeric antibody in the supernatant, like the parent mouse MBr1 antibody, was found to bind to MCF-7 cells but not the HT-29 cells, thus showing that the specificity had been properly cloned and expressed.

EXAMPLE 2

Cloning of Rearranged Variable Genes from Genomic DNA of Mouse Spleen

Preparation of DNA from Spleen.

The DNA from the mouse spleen was prepared in one of two ways (although other ways can be used).

Method 1. A mouse spleen was cut into two pieces and each piece was put into a standard Eppendorf tube with 200 µl of PBS. The tip of a 1 ml glass pipette was closed and rounded in the blue flame of a Bunsen burner. The pipette was used to squash the spleen piece in each tube. The cells thus produced were transferred to a fresh Eppendorf tube and the method was repeated three times until the connective tissue of the spleen appeared white. Any connective tissue which has been transferred with the cells was removed using a drawn-out Pasteur pipette. The cells were then washed in PBS and distributed into four tubes.

The mouse spleen cells were then sedimented by a 2 minute spin in a Microcentaur centrifuge at low speed setting. All the supernatant was aspirated with a drawn out Pasteur pipette. If desired, at this point the cell sample can be frozen and stored at −20° C.

To the cell sample (once thawed if it had been frozen) was added 500 µl of water and 5 µl of a 10% solution of NP-40, a non-ionic detergent. The tube was closed and a hole was punched in the lid. The tube was placed on a boiling water bath for 5 minutes to disrupt the cells and was then cooled on ice for 5 minutes. The tube was then spun for 2 minutes at high speed to remove cell debris.

The supernatant was transferred to a new tube and to this was added 125 µl 5M NaCl and 30 µl 1M MOPS adjusted to pH 7.0. The DNA in the supernatant was absorbed on a Quiagen 5 tip and purified following the manufacturer's instructions for lambda DNA. After isopropanol precipitation, the DNA was resuspended in 500 µl water.

Method 2. This method is based on the technique described in Maniatis et al. [30]. A mouse spleen was cut into very fine pieces and put into a 2 ml glass homogeniser. The cells were then freed from the tissue by several slow up and down strokes with the piston. The cell suspension was made in 500 µl phosphate buffered saline (PBS) and transferred to an Eppendorf tube. The cells were then spun for 2 min at low speed in a Microcentaur centrifuge. This results in a visible separation of white and red cells. The white cells, sedimenting slower, form a layer on top of the red cells. The supernatant was carefully removed and spun to ensure that all the white cells had sedimented. The layer of white cells was resuspended in two portions of 500 µl PBS and transferred to another tube.

The white cells were precipitated by spinning in the Microcentaur centrifuge at low speed for one minute. The cells were washed a further two times with 500 µl PBS, and were finally resuspended in 200 µl PBS. The white cells were added to 2.5 ml 25 mM EDTA and 10 mM Tris.Cl, pH 7.4, and vortexed slowly. While vortexing 25 µl 20% SDS was added. The cells lysed immediately and the solution became viscous and clear. 100 µl of 20 mg/ml proteinase K was added and incubated one to three hours at 50° C.

The sample was extracted with an equal volume of phenol and the same volume of chloroform, and vortexed. After centrifuging, the aqueous phase was removed and 1/10 volume 3M ammonium acetate was added. This was overlaid with three volumes of cold ethanol and the tube rocked carefully until the DNA strands became visible. The DNA was spooled out with a Pasteur pipette, the ethanol allowed to drip off, and the DNA transferred to 1 ml of 10 mM Tris.Cl pH 7.4, 0.1 mM EDTA in an Eppendorf tube. The DNA was allowed to dissolve in the cold overnight on a roller.

Amplification from Genomic DNA.

The DNA solution was diluted 1/10 in water and boiled for 5 min prior to using the polymerase chain reaction (PCR). For each PCR reaction, typically 50-200 ng of DNA were used.

The heavy and light chain variable domain encoding sequences in the genomic DNA isolated from the human PBL or the mouse spleen cells was then amplified and cloned using the general protocol described in the first two paragraphs of the section headed "Amplification from RNA/DNA Hybrid" in Example 1, except that during the annealing part of each cycle, the temperature was held at 65° C. and that 30 cycles were used. Furthermore, to minimise the annealing between the 3' ends of the two primers, the sample was first heated to 95° C., then annealed at 65° C., and only then was the Taq polymerase added. At the end of the 30 cycles, the reaction mixture was held at 60° C. for five minutes to ensure that complete elongation and renaturation of the amplified fragments had taken place.

The primers used to amplify the mouse spleen genomic DNA were VH1FOR and VH1BACK, for the heavy chain variable domain and VK2FOR and VK1BACK, for the light chain variable domain. (VK2FOR only differs from VK1FOR in that it has an extra C residue on the 5' end.)

Other sets of primers, designed to optimise annealing with different families of mouse VH and Vκ genes were devised and used in mixtures with the primers above. For example, mixtures of VK1FOR, MOJK1FOR, MOJK3FOR and MOJK4FOR were used as forward primers and mixtures of VK1BACK, MOVKIIABACK and MOVKIIBBACK as back primers for amplification of Vκ genes. Likewise mixtures of VH1FOR, MOJH1FOR, MOJH2FOR, MOJH3FOR and MOJH4FOR were used as forward primers and mixtures of VH1BACK, MOVHIBACK, MOVHIIABACK, MOVHIIBBACK, MOVHIIIBACK were used as backward primers for amplification of VH genes.

All these heavy chain FOR primers referred to above contain a BstEII site and all the BACK primers referred to above contain a PstI site. These light chain FOR and BACK primers referred to above all contain BglII and PvuII sites respectively. Light chain primers (VK3FOR and VK2BACK) were also devised which utilised different restriction sites, SacI and XhoI.

Typically all these primers yielded amplified DNA of the correct size on gel electrophoresis, although other bands were also present. However, a problem was identified in which the 5' and 3' ends of the forward and backward primers for the VH genes were partially complementary, and this could yield a major band of "primer-dimer" in which the two oligonucleotides prime on each other. For this reason an improved forward primer, VH1FOR-2 was devised in which the two 3' nucleotides were removed from VH1FOR.

Thus, the preferred amplification conditions for mouse VH genes are as follows: the sample was made in a volume of 50-100 µl, 50-100 ng of DNA, VH1FOR-2 and VH1BACK primers (25 pmole of each), 250 µM of each deoxynucleotide triphosphate, 10 mM Tris.HCl, pH 8.8, 50 mM KCl, 1.5 mM $MgCl_2$, and 100 µg/ml gelatine. The sample was overlaid with paraffin oil, heated to 95° C. for 2 min, 65° C. for 2 min, and then to 72° C.: taq polymerase was added after the sample had reached the elongation temperature and the reaction continued for 2 min at 72° C. The sample was subjected to a further 29 rounds of temperature cycling using the Techne PHC-1 programmable heating block.

The preferred amplification conditions for mouse Vκ genes from genomic DNA are as follows: the sample treated as above except with Vκ primers, for example VK3FOR and VK2BACK, and using a cycle of 94° C. for one minute, 60° C. for one minute and 72° C. for one minute.

The conditions which were devised for genomic DNA are also suitable for amplification from the cDNA derived from mRNA from mouse spleen or mouse hybridoma.

Cloning and Analysis of Variable Region Genes

The reaction mixture was then extracted twice with 40 µl of water-saturated diethyl ether. This was followed by a standard phenol extraction and ethanol precipitation as described in Example 1. The DNA pellet was then dissolved in 100 µl 10 mM Tris.Cl, 0.1 mM EDTA.

Each reaction mixture containing a light chain variable domain encoding sequence was digested with SacI and XhoI (or with PvuII and BglII) to enable it to be ligated into a suitable expression vector. Each reaction mixture containing a heavy chain variable domain encoding sequence was digested with PstI and BstEII for the same purpose.

The heavy chain variable genes isolated as above from a mouse hyperimmunised with lysozyme were cloned into M13VHPCR1 vector and sequenced. The complete sequences of 48 VH gene clones were determined (FIG. 10). All but two of the mouse VH gene families were represented, with frequencies of: VA (1), IIIC (1), IIIB (8), IIIA (3), IIB (17), IIA (2), IB (12), IA (4). In 30 clones, the D segments could be assigned to families SP2 (14), FL16 (11) and Q52 (5), and in 38 clones the JH minigenes to families JH1 (3), JH2 (7), JH3 (14) and JH4 (14). The different sequences of CDR3 marked out each of the 48 clones as unique. Nine pseudogenes and 16 unproductive rearrangements were identified. Of the clones sequenced, 27 have open reading frames.

Thus the method is capable of generating a diverse repertoire of heavy chain variable genes from mouse spleen DNA.

EXAMPLE 3

Cloning of Rearranged Variable Genes from mRNA from Human Peripheral Blood Lymphocytes Preparation of mRNA.

Human peripheral blood lymphocytes were purified and mRNA prepared directly (Method 1), or mRNA was prepared after addition of Epstein Barr virus (Method 2).

Method 1. 20 ml of heparinised human blood from a healthy volunteer was diluted with an equal volume of phosphate buffered saline (PBS) and distributed equally into 50 ml Falcon tubes. The blood was then underlayed with 15 ml Ficoll Hypaque (Pharmacia 10-A-001-07). To separate the lymphocytes from the red blood cells, the tubes were spun for 10 minutes at 1800 rpm at room temperature in an IEC Centra 3E table centrifuge. The peripheral blood lymphocytes (PBL) were then collected from the interphase by aspiration with a Pasteur pipette. The cells were diluted with an equal volume of PBS and spun again at 1500 rpm for 15 minutes. The supernatant was aspirated, the cell pellet was resuspended in 1 ml PBS and the cells were distributed into two Eppendorf tubes.

Method 2. 40 ml human blood from a patient with HIV in the pre-AIDS condition was layered on Ficoll to separate the white cells (see Method 1 above). The white cells were then incubated in tissue culture medium for 4-5 days. On day 3, they were infected with Epstein Barr virus. The cells were pelleted (approx $2 \times 10^7$ cells) and washed in PBS.

The cells were pelleted again and lysed with 7 ml 5M guanidine isothiocyanate, 50 mM Tris, 10 mM EDTA, 0.1 mM dithiothreitol. The cells were vortexed vigorously and 7 volumes of 4M LiCl added. The mixture was incubated at 4° C. for 15-20 hrs. The suspension was spun and the supernatant resuspended in 3M LiCl and centrifuged again. The pellet was dissolved in 2 ml 0.1% SDS, 10 mM Tris HCl and 1 mM EDTA. The suspension was frozen at −20° C., and thawed by vortexing for 20 s every 10 min for 45 min. A large white pellet was left behind and the clear supernatant was extracted with phenol chloroform, then with chloroform. The RNA was precipitated by adding 1/10 volume 3M sodium acetate and 2 vol ethanol and leaving overnight at −20° C. The pellet was suspended in 0.2 ml water and reprecipitated with ethanol. Aliquots for cDNA synthesis were taken from the ethanol precipitate which had been vortexed to create a fine suspension.

100 µl of the suspension was precipitated and dissolved in 20 µl water for cDNA synthesis [30] using 10 pmole of a HUFOR primer (see below) in final volume of 50 µl. A sample of 5 µl of the cDNA was amplified as in Example 2 except using the primers for the human VH gene families (see below) using a cycle of 95° C., 60° C. and 72° C.

The back primers for the amplification of human DNA were designed to match the available human heavy and light chain sequences, in which the different families have slightly different nucleotide sequences at the 5' end. Thus for the human VH genes, the primers Hu2VHIBACK, HuVHIIBACK, Hu2VHIIIBACK and HuVH1VBACK were designed as back primers, and HUJH1FOR, HUJH2FOR and HUJH4FOR as forward primers based entirely in the variable gene. Another set of forward primers Hu1VHFOR, Hu2VHFOR, Hu3VHFOR, and Hu4VHFOR was also used, which were designed to match the human J-regions and the 5' end of the constant regions of different human isotopes.

Using sets of these primers it was possible to demonstrate a band of amplified ds cDNA by gel electrophoresis.

One such experiment was analysed in detail to establish whether there was a diverse repertoire in a patient with HIV infection. It is known that during the course of AIDS, that T-cells and also antibodies are greatly diminished in the blood. Presumably the repertoire of lymphocytes is also diminished. In this experiment, for the forward priming, an equimolar mixture of primers Hu1VHFOR, Hu2VHFOR, Hu3VHFOR, and Hu4VHFOR (in PCR 25 pmole of primer 5' ends) was used. For the back priming, the primers Hu2VHIBACK, HuVHIIBACK, Hu2VHIIIBACK and HuVH1VBACK were used separately in four separate primings. The amplified DNA from the separate primings was then pooled, digested with restriction enzymes PstI and BstEII as above, and then cloned into the vector M13VHPCR1 for sequencing. The sequences reveal a diverse repertoire (FIG. 11) at this stage of the disease.

For human Vκ genes the primers HuJK1FOR, HuJK3FOR, HuJK4FOR and HuJK5FOR were used as forward primers and VK1BACK as back primer. Using these primers it was possible to see a band of amplified ds cDNA of the correct size by gel electrophoresis.

EXAMPLE 4

Cloning of Unrearranged Variable Gene Genomic DNA from Human Peripheral Blood Lymphocytes Human peripheral blood lymphocytes of a patient with non-Hodgkins lymphoma were prepared as in Example 3 (Method 1). The genomic DNA was prepared from the PBL using the technique described in Example 2 (Method 2). The VH region in the isolated genomic DNA was then amplified and cloned using the general protocol described in the first two paragraphs of the section headed "Amplification from RNA/DNA hybrid" in Example 1 above, except that during the annealing part of each cycle, the temperature was held at 55° C. and that 30 cycles were used. At the end of the 30 cycles, the reaction mixture was held at 60° C. for five minutes to ensure that complete elongation and renaturation of the amplified fragments had taken place.

The forward primer used was HuHep1FOR, which contains a SacI site. This primer is designed to anneal to the 3' end of the unrearranged human VH region gene, and in particular includes a sequence complementary to the last three codons in the VH region gene and nine nucleotides downstream of these three codons.

As the back primer, an equimolar mixture of HuOcta1BACK, HuOcta2BACK and HuOcta3BACK was used. These primers anneal to a sequence in the promoter region of the genomic DNA VH gene (see FIG. 1). 5 µl of the amplified DNA was checked on 2% agarose gels in TBE buffer and stained with ethidium bromide. A double band was seen of about 620 nucleotides which corresponds to the size expected for the unrearranged VH gene. The ds cDNA was digested with SacI and cloned into an M13 vector for sequencing. Although there are some sequences which are identical, a range of different unrearranged human VH genes were identified (FIG. 12).

EXAMPLE 5

Cloning Variable Domains with Binding Activities from a Hybridoma

The heavy chain variable domain (VHLYS) of the D1.3 (anti-lysozyme) antibody was cloned into a vector similar to that described previously [42] but under the control of the lac z promoter, such that the VHLYS domain is attached to a pelB leader sequence for export into the periplasm. The vector was constructed by synthesis of the pelB leader sequence [43], using overlapping oligonucleotides, and cloning into a pUC 19 vector [35]. The VHLYS domain of the D1.3 antibody was derived from a cDNA clone [44] and the construct (pSW1) sequenced (FIG. 13).

To express both heavy and light chain variable domains together, the light chain variable region (VKLYS) of the D1.3 antibody was introduced into the pSW1 vector, with a pelB signal sequence to give the construct pSW2 (FIG. 14).

A strain of E. coli (BMH71-18) [45] was then transformed [46,47] with the plasmid pSW1 or pSW2, and colonies resistant to ampicillin (100 µg/ml) were selected on a rich (2×TY=per liter of water, 16 g Bacto-tryptone, 10 g yeast extract, 5 g NaCl) plate which contained 1% glucose to repress the expression of variable domain(s) by catabolite repression.

The colonies were inoculated into 50 ml 2×TY (with 1% glucose and 100 µg/ml ampicillin) and grown in flasks at 37° C. with shaking for 12-16 hr. The cells were centrifuged, the pellet washed twice with 50 mM sodium chloride, resuspended in 2×TY medium containing 100 µg/ml ampicillin and the inducer IPTG (1 mM) and grown for a further 30 hrs at 37° C. The cells were centrifuged and the supernatant was passed through a Nalgene filter (0.45 µm) and then down a 1-5 ml lysozyme-Sepharose affinity column. (The column was derived by coupling lysozyme at 10 mg/ml to CNBr activated Sepharose.) The column was first washed with phosphate buffered saline (PBS), then with 50 mM diethylamine to elute the VHLYS domain (from pSW1) or VHLYS in association with VKLYS (from pSW2).

The VHLYS and VKLYS domains were identified by SDS polyacrylamide electrophoresis as the correct size. In addition, N-terminal sequence determination of VHLYS and VKLYS isolated from a polyacrylamide gel showed that the signal peptide had been produced correctly. Thus both the Fv fragment and the VHLYS domains are able to bind to the lysozyme affinity column, suggesting that both retain at least some of the affinity of the original antibody.

The size of the VHLYS domain was compared by FPLC with that of the Fv fragment on Superose 12. This indicates that the VHLYS domain is a monomer. The binding of the VHLYS and Fv fragment to lysozyme was checked by ELISA, and equilibrium and rapid reaction studies were carried out using fluorescence quench.

The ELISA for lysozyme binding was undertaken as follows:

(1) The plates (Dynatech Immulon) were coated with 200 µl per well of 300 µg/ml lysozyme in 50 mM NaHCO$_3$, pH 9.6 overnight at room temperature;
(2) The wells were rinsed with three washes of PBS, and blocked with 300 µl per well of 1% Sainsbury's instant dried skimmed milk powder in PBS for 2 hours at 37° C.;
(3) The wells were rinsed with three washes of PBS and 200 µl of VHLYS or Fv fragment (VHLYS associated with VKLYS) were added and incubated for 2 hours at room temperature;
(4) The wells were washed three times with 0.05% Tween 20 in PBS and then three times with PBS to remove detergent;
(5) 200 µl of a suitable dilution (1:1000) of rabbit polyclonal antisera raised against the FV fragment in 2% skimmed milk powder in PBS was added to each well and incubated at room temperature for 2 hours;
(6) Washes were repeated as in (4);
(7) 200 µl of a suitable dilution (1:1000) of goat anti-rabbit antibody (ICN Immunochemicals) coupled to horse radish peroxidase, in 2% skimmed milk powder in PBS, was added to each well and incubated at room temperature for 1 hour;
(8) Washes were repeated as in (4); and
(9) 200 µl 2,2'azino-bis(3-ethylbenzthiazolinesulphonic acid) [Sigma] (0.55 mg/ml, with 1 µl 20% hydrogen peroxide: water per 10 ml) was added to each well and the colour allowed to develop for up to 10 minutes at room temperature.

The reaction was stopped by adding 0.05% sodium azide in 50 mM citric acid pH 4.3. ELISA plates were read in a Titertek Multiscan plate reader. Supernatant from the induced bacterial cultures of both pSW1 (VHLYS domain) or pSW2 (Fv fragment) was found to bind to lysozyme in the ELISA.

The purified VHLYS and Fv fragments were titrated with lysozyme using fluorescence quench (Perkin Elmer LS5B Luminescence Spectrometer) to measure the stoichiometry of binding and the affinity constant for lysozyme [48,49]. The titration of the Fv fragment at a concentration of 30 nM indicates a dissociation constant of 2.8 nM using a Scatchard analysis.

A similar analysis using fluorescence quench and a Scatchard plot was carried out for VHLYS, at a VHLYS concentration of 100 nM. The stoichiometry of antigen binding is about 1 mole of lysozyme per mole of VHLYS (calculated from plot). (The concentration of VH domains was calculated from optical density at 280 nM using the typical extinction coefficient for complete immunoglobulins.) Due to possible errors in measuring low optical densities and the assumption about the extinction coefficient, the stoichiometry was also measured more carefully. VHLYS was titrated with lysozyme as above using fluorescence quench. To determine the concentration of VHLYS a sample of the stock solution was removed, a known amount of norleucine added, and the sample subjected to quantitative amino acid analysis. This showed a stoichiometry of 1.2 mole of lysozyme per mole of VHLYS domain. The dissociation constant was calculated as about 12 nM.

The on-rates for VHLYS and Fv fragments with lysozyme were determined by stopped-flow analysis (HI Tech Stop Flow SHU machine) under pseudo-first order conditions with the fragment at a ten fold higher concentration than lysozyme [50]. The concentration of lysozyme binding sites was first measured by titration with lysozyme using fluorescence quench as above. The on rates were calculated per mole of binding site (rather than amount of VHLYS protein). The on-rate for the Fv fragment was found to be $2.2 \times 10^6$ $M^{-1} s^{-1}$ at 25° C. The on-rate for the VHLYS fragment found to be $3.8 \times 10^6 M^{-1} s^{-1}$ and the off-rate $0.075 s^{-1}$ at 20° C. The calculated affinity constant is 19 nM. Thus the VHLYS binds to lysozyme with a dissociation constant of about 19 nM, compared with that of the Fv of 3 nM.

EXAMPLE 6

Cloning Complete Variable Domains with Binding Activities from mRNA or DNA of Antibody-secreting Cells A mouse was immunised with hen egg white lysozyme (100 μg i.p. day 1 in complete Freunds adjuvant), after 14 days immunised i.p. again with 100 μg lysozyme with incomplete Freunds adjuvant, and on day 35 i.v. with 50 μg lysozyme in saline. On day 39, spleen was harvested. A second mouse was immunised with keyhole limpet haemocyanin (KLH) in a similar way. The DNA was prepared from the spleen according to Example 2 (Method 2). The VH genes were amplified according to the preferred method in Example 2.

Human peripheral blood lymphocytes from a patient infected with HIV were prepared as in Example 3 (Method 2) and mRNA prepared. The VH genes were amplified according to the method described in Example 3, using primers designed for human VH gene families.

After the PCR, the reaction mixture and oil were extracted twice with ether, once with phenol and once with phenol/CHCl$_3$. The double stranded DNA was then taken up in 50 μl of water and frozen. 5 μl was digested with PstI and BstEII (encoded within the amplification primers) and loaded on an agarose gel for electrophoresis. The band of amplified DNA at about 350 bp was extracted.

Expression of Anti-lysozyme Activities

The repertoire of amplified heavy chain variable domains (from mouse immunised with lysozyme and from human PBLs) was then cloned directly into the expression vector pSW1HPOLYMYC. This vector is derived from pSW1 except that the VHLYS gene has been removed and replaced by a polylinker restriction site. A sequence encoding a peptide tag was inserted (FIG. 15). Colonies were toothpicked into 1 ml cultures. After induction (see Example 5 for details), 10 μl of the supernatant from fourteen 1 ml cultures was loaded on SDS-PAGE gels and the proteins transferred electrophoretically to nitrocellulose. The blot was probed with antibody 9E10 directed against the peptide tag.

The probing was undertaken as follows. The nitrocellulose filter was incubated in 3% bovine serum albumin (BSA)/TBS buffer for 20 min (10×TBS buffer is 100 mM Tris.HCl, pH 7.4, 9% w/v NaCl). The filter was incubated in a suitable dilution of antibody 9E10 (about 1/500) in 3% BSA/TBS for 1-4 hrs. After three washes in TBS (100 ml per wash, each wash for 10 min), the filter was incubated with 1:500 dilution of anti-mouse antibody (peroxidase conjugated anti-mouse Ig (Dakopats)) in 3% BSA/TBS for 1-2 hrs. After three washes in TBS and 0.1% Triton X-100 (about 100 ml per wash, each wash for 10 min), a solution containing 10 ml chloronapthol in methanol (3 mg/ml), 40 ml TBS and 50 μl hydrogen peroxide solution was added over the blot and allowed to react for up to 10 min. The substrate was washed out with excess water. The blot revealed bands similar in mobility to VHLYSMYC on the Western blot, showing that other VH domains could be expressed.

Colonies were then toothpicked individually into wells of an ELISA plate (200 μl) for growth and induction. They were assayed for lysozyme binding with the 9E10 antibody (as in Examples 5 and 7). Wells with lysozyme-binding activity were identified. Two positive wells (of 200) were identified from the amplified mouse spleen DNA and one well from the human cDNA. The heavy chain variable domains were purified on a column of lysozyme-Sepharose. The affinity for lysozyme of the clones was estimated by fluorescence quench titration as >50 nM. The affinities of the two clones (VH3 and VH8) derived from the mouse genes were also estimated by stop flow analysis (ratio of $k_{on}/k_{off}$) as 12 nM and 27 nM respectively. Thus both these clones have a comparable affinity to the VHLYS domain. The encoded amino acid sequences of VH3 and VH8 are given in FIG. 16, and that of the human variable domain in FIG. 17.

A library of VH domains made from the mouse immunised with lysozyme was screened for both lysozyme and keyhole limpet haemocyanin (KLH) binding activities. Two thousand colonies were toothpicked in groups of five into wells of ELISA plates, and the supernatants tested for binding to lysozyme coated plates and separately to KLH coated plates. Twenty one supernatants were shown to have lysozyme binding activities and two to have KLH binding activities. A second expression library, prepared from a mouse immunised with KLH was screened as above. Fourteen supernatants had KLH binding activities and a single supernatant had lysozyme binding activity.

This shows that antigen binding activities can be prepared from single VH domains, and that immunisation facilitates the isolation of these domains.

EXAMPLE 7

Cloning Variable Domains with Binding Activities by Mutagenesis.

Taking a single rearranged VH gene, it may be possible to derive entirely new antigen binding activities by extensively mutating each of the CDRs. The mutagenesis might be entirely random, or be derived from pre-existing repertoires of CDRs. Thus a repertoire of CDR3s might be prepared as in the preceding examples by using "universal" primers based in the flanking sequences, and likewise repertoires of the other CDRs (singly or in combination). The CDR repertoires could be stitched into place in the flanking framework regions by a variety of recombinant DNA techniques.

CDR3 appears to be the most promising region for mutagenesis as CDR3 is more variable in size and sequence than CDRs 1 and 2. This region would be expected to make a major contribution to antigen binding. The heavy chain variable region (VHLYS) of the anti-lysozyme antibody D1.3 is known to make several important contacts in the CDR3 region.

Multiple mutations were made in CDR3. The polymerase chain reaction (PCR) and a highly degenerate primer were used to make the mutations and by this means the original sequence of CDR3 was destroyed. (It would also have been possible to construct the mutations in CDR3 by cloning a mixed oligonucleotide duplex into restriction sites flanking the CDR or by other methods of site-directed mutagenesis). Mutants expressing heavy chain variable domains with affinities for lysozyme were screened and those with improved affinities or new specificities were identified.

The source of the heavy chain variable domain was an M13 vector containing the VHLYS gene. The body of the sequence encoding the variable region was amplified using the polymerase chain reaction (PCR) with the mutagenic primer VHMUT1 based in CDR3 and the M13 primer which is based in the M13 vector backbone. The mutagenic primer hypermutates the central four residues of CDR3 (Arg-Asp-Tyr-Arg). The PCR was carried out for 25 cycles on a Techne PHC-1 programmable heat block using 100 ng single stranded M13mp19SWO template, with 25 pmol of VHMUT1 and the M13 primer, 0.5 mM each dNTP, 67 mM Tris.HCl, pH 8.8, 10 mM MgCl2, 17 mM (NH$_4$)$_2$SO$_4$, 200 µg/ml gelatine and 2.5 units Taq polymerase in a final volume of 50 µl. The temperature regime was 95° C. for 1.5 min, 25° C. for 1.5 min and 72° C. for 3 min (However a range of PCR conditions could be used). The reaction products were extracted with phenol/chloroform, precipitated with ethanol and resuspended in 10 mM Tris. HCl and 0.1 mM EDTA, pH 8.0.

The products from the PCR were digested with PstI and BstEII and purified on a 1.5% LGT agarose gel in Tris acetate buffer using Geneclean (Bio 101, LaJolla). The gel purified band was ligated into pSW2HPOLY (FIG. 19). (This vector is related to pSW2 except that the body of the VHLYS gene has been replaced by a polylinker.) The vector was first digested with BstEII and PstI and treated with calf-intestinal phosphatase. Aliquots of the reaction mix were used to transform *E. coli* BMH 71-18 to ampicillin resistance. Colonies were selected on ampicillin (100 µg/ml) rich plates containing glucose at 0.8% w/v.

Colonies resulting from transfection were picked in pools of five into two 96 well Corning microtitre plates, containing 200 µl 2×TY medium and 100 µl TY medium, 100 µg/ml ampicillin and 1% glucose. The colonies were grown for 24 hours at 37° C. and then cells were washed twice in 200 µl 50 mM NaCl, pelleting the cells in an IEC Centra-3 bench top centrifuge with microtitre plate head fitting. Plates were spun at 2,500 rpm for 10 min at room temperature. Cells were resuspended in 200 µl 2×TY, 100 µg/ml ampicillin and 1 mM IPTG (Sigma) to induce expression, and grown for a further 24 hr.

Cells were spun down and the supernatants used in ELISA with lysozyme coated plates and anti-idiotypic sera (raised in rabbits against the Fv fragment of the D1.3 antibody). Bound anti-idiotypic serum was detected using horse radish peroxidase conjugated to anti-rabbit sera (ICN Immunochemicals). Seven of the wells gave a positive result in the ELISA. These pools were restreaked for single colonies which were picked, grown up, induced in microtitre plates and rescreened in the ELISA as above. Positive clones were grown up at the 50 ml scale and expression was induced. Culture supernatants were purified as in Example 5 on columns of lysozyme-Sepharose and eluates analysed on SDS-PAGE and staining with Page Blue 90 (BDH). On elution of the column with diethylamine, bands corresponding to the VHLYS mutant domains were identified, but none to the VKLYS domains. This suggested that although the mutant domains could bind to lysozyme, they could no longer associate with the VKYLS domains.

For seven clones giving a positive reaction in ELISA, plasmids were prepared and the VKLYS gene excised by cutting with EcoRI and religating. Thus the plasmids should only direct the expression of the VHLYS mutants. 1.5 ml cultures were grown and induced for expression as above. The cells were spun down and supernatant shown to bind lysozyme as above. (Alternatively the amplified mutant VKLYS genes could have been cloned directly into the pSW1HPOLY vector for expression of the mutant activities in the absence of VKLYS.)

An ELISA method was devised in which the activities of bacterial supernatants for binding of lysozyme (or KLH) were compared. Firstly a vector was devised for tagging of the VH domains at its C-terminal region with a peptide from the c-myc protein which is recognised by a monoclonal antibody 9E10. The vector was derived from psW1 by a BstEII and SmaI double digest, and ligation of an oligonucleotide duplex made from 5' GTC ACC GTC TCC TCA GAA CAA AAA CTC ATC TCA GAA GAG GAT CTG AAT TAA TAA 3' and
5' TTA TTA ATT CAG ATC CTC TTC TGA GAT GAG TTT TTG TTC TGA GGA GAC G 3'.

The VHLYSMYC protein domain expressed after induction was shown to bind to lysozyme and to the 9E10 antibody by ELISA as follows:

(1) Falcon (3912) flat bottomed wells were coated with 180 µl lysozyme (3 mg/ml) or KLH (50 µg/ml) per well in 50 mM NaHCO3, pH 9.6, and left to stand at room temperature overnight;

(2) The wells were washed with PBS and blocked for 2 hrs at 37° C. with 200 µl 2% Sainsbury's instant dried skimmed milk powder in PBS per well;

(3) The Blocking solution was discarded, and the walls washed out with PBS (3 washes) and 150 µl test solution (supernatant or purified tagged domain) pipetted into each well. The sample was incubated at 37° C. for 2 hrs;

(4) The test solution was discarded, and the wells washed out with PBS (3 washes). 100 µl of 4 µg/ml purified 9E10 antibody in 2% Sainsbury's instant dried skimmed milk powder in PBS was added, and incubated at 37° C. for 2 hrs;

(5) The 9E10 antibody was discarded, the wells washed with PBS (3 washes). 100 µl of 1/500 dilution of anti-mouse antibody (peroxidase conjugated anti-mouse Ig (Dakopats)) was added and incubated at 37° C. for 2 hrs;

(6) The second antibody was discarded and wells washed three times with PBS; and (7) 100 µl 2,2'azino-bis(3-ethylbenzthiazolinesulphonic acid) [Sigma] (0.55 mg/ml, with 1 µl 20% hydrogen peroxide: water per 10 ml) was added to each well and the colour allowed to develop for up to 10 minutes at room temperature.

The reaction was stopped by adding 0.05% sodium azide in 50 mM citric acid, pH 4.3. ELISA plates were read in an Titertek Multiscan plate reader.

The activities of the mutant supernatants were compared with VHLYS supernatant by competition with the VHLYS-MYC domain for binding to lysozyme. The results show that supernatant from clone VHLYSMUT59 is more effective than wild type VHLYS supernatant in competing for VHLYSMYC. Furthermore, Western blots of SDS-PAGE aliquots of supernatant from the VHLYS and VHLYSMUT59 domain (using anti-Fv antisera) indicated comparable amounts of the two samples. Thus assuming identical amounts of VHLYS and VHLYSMUT59, the affinity of the mutant appears to be greater than that of the VHLYS domain.

To check the affinity of the VHLYSMUT59 domain directly, the clone was grown at the 1 l scale and 200-300 µg purified on lysozyme-Sepharose as in Example 5. By fluorescence quench titration of samples of VHLYS and VHLYSMUT59, the number of binding sites for lysozyme were determined. The samples of VHLYS and VHLYSMUT59 were then compared in the competition ELISA with VHLYSMYC over two orders of magnitude. In the competition assay each microtitre well contained a constant amount of VHLYSMYC (approximately 0.6 µg VHLYSMYC). Varying amounts of VHLYS or VHLYSMUT59 (3.8 µM in lysozyme binding sites) were added (0.166-25 µl). The final volume and buffer concentration in all wells was constant. 9E10 (anti-myc) antibody was used to quantitate bound VHLYSMYC in each assay well. The % inhibition of VHLYSMYC binding was calculated for each addition of VHLYS or VHLYSMUT59, after subtraction of background binding. Assays were carried out in duplicate. The results indicate that VHLYSMUT59 has a higher affinity for lysozyme than VHLYS.

The VHLYSMUT59 gene was sequenced (after recloning into M13) and shown to be identical to the VHLYS gene except for the central residues of CDR3 (Arg-Asp-Tyr-Arg). These were replaced by Thr-Gln-Arg-Pro: (encoded by ACACAAAGGCCA).

A library of 2000 mutant VH clones was screened for lysozyme and also for KLH binding (toothpicking 5 colonies per well as described in Example 6). Nineteen supernatants were identified with lysozyme binding activities and four with KLH binding activities. This indicates that new specificites and improved affinities can be derived by making a random repertoire of CDR3.

EXAMPLE 8

Construction and Expression of Double Domain for Lysozyme Binding.

The finding that single domains have excellent binding activities should allow the construction of strings of domains (concatamers). Thus, multiple specificities could be built into the same molecule, allowing binding to different epitopes spaced apart by the distance between domain heads. Flexible linker regions could be built to space out the domains. In principle such molecules could be devised to have exceptional specificity and affinity.

Two copies of the cloned heavy chain variable gene of the D1.3 antibody were linked by a nucleotide sequence encoding a flexible linker Gly-Gly-Gly-Ala-Pro-Ala-Ala-Ala-Pro-Ala-Gly-Gly-Gly- (by several steps of cutting, pasting and site directed mutagenesis) to yield the plasmid pSW3 (FIG. 20). The expression was driven by a lacz promoter and the protein was secreted into the periplasm via a pelB leader sequence (as described in Example 5 for expression of pSW1 and pSW2). The protein could be purified to homogeneity on a lysozyme affinity column. On SDS polyacrylamide gels, it gave a band of the right size (molecular weight about 26,000). The protein also bound strongly to lysozyme as detected by ELISA (see Example 5) using anti-idiotypic antiserum directed against the Fv fragment of the D1.3 antibody to detect the protein. Thus, such constructs are readily made and secreted and at least one of the domains binds to lysozyme.

EXAMPLE 9

Introduction of Cysteine Residue at C-terminal End of VHLYS

A cysteine residue was introduced at the C-terminus of the VHLYS domain in the vector pSW2. The cysteine was introduced by cleavage of the vector with the restriction enzymes BstI and SmaI (which excises the C-terminal portion of the J segment) and ligation of a short oligonucleotide duplex 5' GTC ACC GTC TCC TCA TGT TAA TAA 3' and 5' TTA TTA ACA TGA GGA GAC G 3'. By purification on an affinity column of lysozyme Sepharose it was shown that the VHLYS-Cys domain was expressed in association with the VKLYS variable domain, but the overall yields were much lower than the wild type Fv fragment. Comparison of non-reducing and reducing SDS polyacrylamide gels of the purified Fv-Cys protein indicated that the two VH-Cys domains had become linked-through the introduced cysteine residue.

EXAMPLE 10

Linking of VH Domain with Enzyme

Linking of enzyme activities to VH domains should be possible by either cloning the enzyme on either the N-terminal or the C-terminal side of the VH domain. Since both partners must be active, it may be necessary to design a suitable linker (see Example 8) between the two domains. For secretion of the VH-enzyme fusion, it would be preferable to utilise an enzyme which is usually secreted. In FIG. 21, there is shown the sequence of a fusion of a VH domain with alkaline phosphatase. The alkaline phosphatase gene was cloned from a plasmid carrying the E. coli alkaline phosphatase gene in a plasmid pEK48 [51] using the polymerase chain reaction. The gene was amplified with the primers 5' CAC CAC GGT CAC CGT CTC CTC ACG GAC ACC AGA AAT GCC TGT TCT G 3' and 5' GCG AAA ATT CAC TCC CGG GCG CGG TTT TAT TTC 3'. The gene was introduced into the vector pSW1 by cutting at BstEII and SmaI. The construction (FIG. 21) was expressed in E. coli strain BMH71-18 as in Example 5 and screened for phosphatase activity using 1 mg/ml p-nitrophenylphosphate as substrate in 10 mM diethanolamine and 0.5 mM $MgCl^2$, pH 9.5) and also on SDS polyacrylamide gels which had been Western blotted (detecting with anti-idiotypic antiserum). No evidence was found for the secretion of the linked VHLYS-alkaline phosphatase as detected by Western blots (see Example 5), or for secretion of phosphatase activity.

However when the construct was transfected into a bacterial strain BL21DE3 [52] which is deficient in proteases, a band of the correct size (as well as degraded products) was detected on the Western blots. Furthermore phosphatase activity could now be detected in the bacterial supernatant. Such activity is not present in supernatant from the strain which had not been transfected with the construct.

A variety of linker sequences could then be introduced at the BstEII site to improve the spacing between the two domains.

EXAMPLE 11

Coexpression of VH Domains with Vκ Repertoire

A repertoire of Vκ genes was derived by PCR using primers as described in Example 2 from DNA prepared from mouse spleen and also from mouse spleen mRNA using the primers VK3FOR and VK2BACK and a cycle of 94° C. for 1 min, 60° C. for 1 min, 72° C. for 2 min. The PCR amplified DNA was fractionated on the agarose gel, the band excised and cloned into a vector which carries the VHLYS domain (from the D1.3 antibody), and a cloning site (SacI and XhoI) for cloning of the light chain variable domains with a myc tail (PSW1VHLYS-VKPOLYMYC, FIG. 22).

Clones were screened for lysozyme binding activities as described in Examples 5 and 7 via the myc tag on the light chain variable domain, as this should permit the following kinds of Vκ domains to be identified:

(1) those which bind to lysozyme in the absence of the VHLYS domain;
(2) those which associate with the heavy chain and make no contribution to binding of lysozyme; and
(3) those which associate with the heavy chain and also contribute to binding of lysozyme (either helping or hindering).

This would not identify those Vκ domains which associated with the VHLYS domain and completely abolished its binding to lysozyme.

In a further experiment, the VHLYS domain was replaced by the heavy chain variable domain VH3 which had been isolated from the repertoire (see Example 6), and then the Vκ domains cloned into the vector. (Note that the VH3 domain has an internal SacI site and this was first removed to allow the cloning of the Vκ repertoire as SacI-XhoI fragments.)

By screening the supernatant using the ELISA described in Example 6, bacterial supernatants will be identified which bind lysozyme.

EXAMPLE 12

High Expression of VH Domains.

By screening several clones from a VH library derived from a mouse immunised with lysozyme via a Western blot, using the 9E10 antibody directed against the peptide tag, one clone was noted with very high levels of expression of the domain (estimated as 25-50 mg/l). The clone was sequenced to determine the nature of the sequence. The sequence proved to be closely related to that of the VHLYS domain, except with a few amino acid changes (FIG. 23). The result was unexpected, and shows that a limited number of amino acid changes, perhaps even a single amino acid substitution, can cause greatly elevated levels of expression.

By making mutations of the high expressing domain at these residues, it was found that a single amino acid change in the VHLYS domain (Asn 35 to His) is sufficient to cause the domain to be expressed at high levels.

CONCLUSION

It can thus be seen that the present invention enables the cloning, amplification and expression of heavy and light chain variable domain encoding sequences in a much more simple manner than was previously possible. It also shows that isolated variable domains or such domains linked to effector molecules are unexpectedly useful.

It will be appreciated that the present invention has been described above by way of example only and that variations and modifications may be made by the skilled person without departing from the scope of the invention.

LIST OF REFERENCES

[1] Inbar et al., PNAS-USA, 69, 2659-2662, 1972.
[2] Amit et al., Science, 233, 747, 1986.
[3] Satow et al., J. Mol. Biol., 190, 593, 1986.
[4] Colman et al., Nature, 326, 358, 1987.
[5] Sheriff et al., PNAS-USA, 84, 8075-8079, 1987.
[6] Padlan et al., PNAS-USA, 86, 5938-5942, 1989.
[7] Skerra and Plückthun, Science, 240, 1038-1041, 1988.
[8] Bird et al., Science, 242, 423-426, 1988.
[9] Huston et al., PNAS-USA, 85, 5879-5833, 1988.
[10] Fleischman, Arch. Biochem. Biophys. Suppl., 1, 174, 1966.
[11] Porter and Weir, J. Cell. Physiol. Suppl., 1, 51, 1967.
[12] Jaton et al., Biochemistry, 7, 4185, 1968.
[13] Rockey, J. Exp. Med., 125, 249, 1967.
[14] Stevenson, Biochem. J., 133, 827-836, 1973.
[15] Edmundson et al., Biochemistry, 14, 3953, 1975.
[16] Rossman et al., Nature, 317, 145-153, 1985.
[17] Saiki et al., Science, 230, 1350-1354, 1985.
[18] Larrick et al., Biochem. Biophys. Res. Comm., 160, 1250, 1989.
[19] Orlandi et al., PNAS-USA, 86, 3833, 1989.
[20] Yon and Fried, Nuc. Acids Res., 17, 4895, 1989.
[21] Fields and Song, Nature, 340, 245-246, 1989.
[22] Baldwin and Schultz, Science, 245, 1104-1107, 1989.
[23] Menard et al., Cancer Res., 43, 1295-1300, 1983.
[24] Bosslet et al., Eur. J. Nuc. Med., 14, 523-528, 1988.
[25] Bosslet et al., Cancer Immunol. Immunother., 23, 185-191, 1986.
[26] Bosslet et al., Int. J. Cancer, 36, 75-84, 1985.
[27]
[28] Bremer et al., J. Biol. Chem., 259, 14773-14777, 1984.
[29] Griffiths & Milstein, Hybridoma Technology in the Biosciences and Medicine, 103-115, 1985.
[30] Maniatis et al., Molecular Cloning: a Laboratory Manual, Cold Spring Harbour Laboratory, 1982.
[31] Jones et al., Nature, 321, 522-525, 1986.
[32] Zoller & Smith, Nuc. Acids Res., 10, 6457-6500, 1982.
[33] Carter et al., Nuc. Acids Res., 13, 4431-4443, 1985.
[34] Sanger et al., PNAS-USA, 74, 5463-5467, 1977.
[35] Yannisch-Perron et al., Gene, 33, 103-119, 1985.
[36]
[37] Riechmann et al., Nature, 332, 323-327, 1988.
[38] Kearney et al., J. Immunol., 123, 1548-1550, 1979.
[39] Potter et al., PNAS-USA, 81, 7161-7163, 1984.
[40] Galfre & Milstein, Meth. Enzym., 73, 1-46, 1981.
[41] Laemmli, Nature, 227, 680-685, 1970.
[42] Better et al., Science, 240, 1041, 1988.
[43] Lei et al., J. Bacteriol., 169, 4379, 1987.
[44] Verhoeyen et al., Science, 239, 1534, 1988.
[45] Gronenborn, Mol. Gen. Genet, 148, 243, 1976.
[46] Dagert et al., Gene, 6, 23, 1974.
[47] Hanahan, J. Mol. Biol., 166, 557, 1983.
[48] Jones et al., Nature, 321, 522, 1986.
[49] Segal, Enzyme Kinetics, 73, Wiley, New York, 1975.
[50] Gutfreund, Enzymes, Physical Principles, Wiley Interscience, London, 1972.
[51] Chaidaroglou, Biochem., 27, 8338, 1988.
[52] Grodberg and Dunn, J. Bacteriol., 170, 1245-1253, 1988.

The invention claimed is:

1. A method for making an antibody to a target antigen which method comprises:
    (a) generating an antibody variable domain expression library having a diversity of CDR3 sequences by a method comprising:
        (i) providing expression vectors, said vectors comprising a variable domain encoding sequence of an antibody;
        (ii) introducing by mutagenesis a diversity of CDR3 sequences into said variable domain encoding sequence;
        (iii) recovering an expression library having a diversity of CDR3 binding activities; and
        (iv) selecting a vector encoding an antibody variable domain having binding activity against the target antigen from said library;
    (b) constructing a vector encoding an antibody comprising said selected antibody variable domain attached to an antibody chain constant domain; and
    (c) expressing said antibody in a mammalian cell.

2. The method of claim 1 wherein said expression library having a diversity of CDR3 sequences is a VH domain library.

3. The method of claim 2 wherein said antibody chain constant domain is a heavy chain constant domain.

4. The method of claim 3 wherein said expressing in a mammalian cell is in association with a light chain to provide a complete antibody.

5. A method for making an antibody to a target antigen which method comprises
  (a) providing an antibody variable domain encoding sequence selected from an expression library made by a method comprising:
    (i) providing expression vectors, said vectors comprising a variable domain encoding sequence of an antibody;
    (ii) introducing by mutagenesis a diversity of CDR3 sequences into said variable domain encoding sequence;
    (iii) recovering an expression library having a diversity of CDR3 binding activities;
  (b) constructing a vector encoding an antibody comprising said selected antibody variable domain encoding sequence attached to an antibody chain constant domain encoding sequence; and
  (c) expressing said antibody in a mammalian cell.

6. A method for obtaining an antibody to a target antigen which method comprises:
  (a) providing an expression library which expresses antibody variable domains, said library comprising a universal set of framework regions carrying a diversity of CDR3 sequences, said library having a diversity of binding activities,
  (b) selecting from said library an antibody variable domain encoding sequence which encodes a variable domain which binds to said target antigen; and
  (c) expressing said sequence attached to an antibody chain constant domain encoding region in a mammalian cell.

7. The method of claim 6 wherein said expression library having a diversity of CDR3 sequences is a VH library.

8. The method of claim 7 wherein said antibody chain constant domain is a heavy chain constant domain.

9. The method of claim 8 wherein said expressing in a mammalian cell is in association with a light chain to provide a complete antibody.

* * * * *

UNITED STATES PATENT AND TRADEMARK OFFICE
CERTIFICATE OF CORRECTION

PATENT NO. : 7,306,907 B2  
APPLICATION NO. : 10/290252  
DATED : December 11, 2007  
INVENTOR(S) : Winter et al.

Page 1 of 1

It is certified that error appears in the above-identified patent and that said Letters Patent is hereby corrected as shown below:

On the Title Page, item (60): delete "Continuation of application No. 09/722,364, filed on Nov. 28, 2000, now Pat. No. 6,545,142, which is a continuation of application No. 08/470,031, filed on Jun. 6, 1995, now Pat. No. 6,248,516, which is a divisional of application No. 08/332,046, filed Nov. 1, 1994, now abandoned, which is a continuation of application No. 07/796,805, filed Nov. 25, 1991, now abandoned, which is a division of application No. 07/580,374, filed Sep. 11, 1990, now abandoned.", and insert therefor --Continuation of application No. 09/722,364, filed on Nov. 28, 2000, now Pat. No. 6,545,142, which is a continuation of application No. 08/470,031, filed on Jun. 6, 1995, now Pat. No. 6,248,516, which is a divisional of application No. 08/332,046, filed Nov. 1, 1994, now abandoned, which is a continuation of application No. 07/796,805, filed Nov. 25, 1991, now abandoned, which is a division of application No. 07/580,374, filed Sep. 11, 1990, now abandoned, which is a continuation of application no. PCT/GB89/01344, filed Nov. 13, 1989.--

On the Title Page, item (30), delete the following last line: "Nov 13, 1989 (WO) PCT/GB89/01344"

Column 1, lines 6-15, delete the following: "This is a continuation of application Ser. No. 09/722,364, filed on Nov. 28, 2000, now U.S. Pat. No. 6,545,142, which is a continuation of application Ser. No. 08/470,031, filed Jun. 6, 1995, now U.S. Pat. No. 6,248,516 on Jun. 19, 2001, which is a divisional of Ser. No. 08/332,046, filed Nov. 1, 1994 now abandoned; which is a continuation of Ser. No. 07/796,805, filed Nov. 25, 1991 now abandoned, which is a divisional of Ser. No. 07/580,374, filed Sep. 11, 1990, abandoned the entire content of each of which is hereby incorporate by reference in this application." and insert the following therefor: --This is a continuation of application Ser. No. 09/722,364, filed on Nov. 28, 2000, now U.S. Pat. No. 6,545,142, which is a continuation of application Ser. No. 08/470,031, filed Jun. 6, 1995, now U.S. Pat. No. 6,248,516 on Jun. 19, 2001, which is a divisional of Ser. No. 08/332,046, filed Nov. 1, 1994 now abandoned; which is a continuation of Ser. No. 07/796,805, filed Nov. 25, 1991 now abandoned, which is a divisional of Ser. No. 07/580,374, filed Sep. 11, 1990, abandoned, which is a continuation of application no. PCT/GB89/01344, filed Nov. 13, 1989.--

Signed and Sealed this  
Fourteenth Day of February, 2012

David J. Kappos  
*Director of the United States Patent and Trademark Office*